(12) United States Patent
Depla et al.

(10) Patent No.: US 11,007,146 B2
(45) Date of Patent: May 18, 2021

(54) METHODS AND COMPOSITIONS FOR THE PREPARATION OF AEROSOLS

(71) Applicant: Ablynx N.V., Zwijnaarde (BE)

(72) Inventors: Erik Depla, Destelbergen (BE); Mauro Sergi, Kufstein (AT); Peter Casteels, Erpe-Mere (BE)

(73) Assignee: Ablynx N.V., Ghent-Zwijnaarde (BE)

( * ) Notice: Subject to any disclaimer, the term of this patent is extended or adjusted under 35 U.S.C. 154(b) by 565 days.

(21) Appl. No.: 15/495,199

(22) Filed: Apr. 24, 2017

(65) Prior Publication Data

US 2017/0333344 A1    Nov. 23, 2017

Related U.S. Application Data

(63) Continuation of application No. 13/577,961, filed as application No. PCT/EP2011/052024 on Feb. 11, 2011, now Pat. No. 9,713,589.

(60) Provisional application No. 61/426,610, filed on Dec. 23, 2010, provisional application No. 61/303,447, filed on Feb. 11, 2010.

(51) Int. Cl.
*A61K 39/395* (2006.01)
*A61K 9/00* (2006.01)
*A61K 47/10* (2017.01)
*A61K 47/26* (2006.01)

(52) U.S. Cl.
CPC ............ *A61K 9/0078* (2013.01); *A61K 47/10* (2013.01); *A61K 47/26* (2013.01)

(58) Field of Classification Search
None
See application file for complete search history.

(56) References Cited

U.S. PATENT DOCUMENTS

| 5,586,550 A | 12/1996 | Ivri et al. |
| 5,758,637 A | 6/1998 | Ivri et al. |
| 5,938,117 A | 8/1999 | Ivri |

(Continued)

FOREIGN PATENT DOCUMENTS

| CN | 101600457 A | 9/2009 |
| JP | 2006-519763 | 8/2006 |

(Continued)

OTHER PUBLICATIONS

Shimizu et al., "Drug Atomization with Vibrating Mesh Nebulizer for Dry Eye and Allergy Deseases," Paper ID ICLASS06-256 (Year: 2006).*

(Continued)

*Primary Examiner* — M Franco G Salvoza
(74) *Attorney, Agent, or Firm* — Wolf, Greenfield & Sacks, P.C.

(57) ABSTRACT

The present invention relates to methods for the preparation of an aerosol. More specifically the present invention provides methods for the preparation of an aerosol of immunoglobulin single variable domains wherein the amount of aggregate formation is significantly reduced. The invention further provides aerosols prepared by the methods of the invention, as well as compositions for use in the methods of the invention. The invention further relates to methods for the preparations of such compositions, to containers, kits and aerosol delivery systems comprising such compositions and to uses of the same.

4 Claims, 9 Drawing Sheets

Specification includes a Sequence Listing.

(56) References Cited

U.S. PATENT DOCUMENTS

| | | |
|---|---|---|
| 5,945,098 A | 8/1999 | Sarno et al. |
| 6,014,970 A | 1/2000 | Ivri et al. |
| 6,085,740 A | 7/2000 | Ivri et al. |
| 6,205,999 B1 | 3/2001 | Ivri et al. |
| 9,713,589 B2 | 7/2017 | Depla et al. |
| 2009/0060916 A1* | 3/2009 | De Silva .............. C07K 16/247 424/139.1 |

FOREIGN PATENT DOCUMENTS

| | | |
|---|---|---|
| JP | 2011-506396 | 3/2011 |
| JP | 6283064 B2 | 2/2018 |
| WO | WO 04/041867 A2 | 5/2004 |
| WO | WO 04/062551 A2 | 7/2004 |
| WO | WO 05/044858 A1 | 5/2005 |
| WO | WO 06/040153 A2 | 4/2006 |
| WO | WO 06/122257 A2 | 11/2006 |
| WO | WO 06/122825 A2 | 11/2006 |
| WO | WO 07/104529 A2 | 9/2007 |
| WO | WO 08/020079 A1 | 2/2008 |
| WO | WO 08/049897 A1 | 5/2008 |
| WO | WO 08/071447 A2 | 6/2008 |
| WO | WO 08/074839 A2 | 6/2008 |
| WO | WO 08/074840 A2 | 6/2008 |
| WO | WO 08/074867 A2 | 6/2008 |
| WO | WO 08/077945 A2 | 7/2008 |
| WO | WO 08/086395 A2 | 7/2008 |
| WO | WO 08/101985 A2 | 8/2008 |
| WO | WO 08/142164 A2 | 11/2008 |
| WO | WO 08/142165 A1 | 11/2008 |
| WO | WO 09/068625 A2 | 6/2009 |
| WO | WO 09/068627 A2 | 6/2009 |
| WO | WO 09/074634 A2 | 6/2009 |
| WO | WO 11/026945 A1 | 3/2011 |
| WO | WO 11/026948 A1 | 3/2011 |

OTHER PUBLICATIONS

PCT/EP2011/052024, dated Feb. 9, 2012, International Search Report and Written Opinion.

PCT/EP2011/052024, dated Aug. 23, 2012, International Preliminary Report on Patentability.

WO 2008/086395 is an English equivalent of CN 101600457.

WO 2009/074634 is the English equivalent for JP 2011-506396.

[No Author Listed] Nebulizer. Wikipedia article. Last modified on Sep. 13, 2009. http://en.wikipedia.org/wiki/Nebulizer. Downloaded on Jan. 18, 2010. 2 pages.

Andrews, Partial denaturation and renaturation of beta-lactoglobulin at air-water interfaces. Biochem Soc Trans. Aug. 1991;19(3):272S.

Beaucage et al., Using inhalation devices. Comprehensive management of chronic obstructive pulmonary disease. 2002. Chapter 6. 83-107.

Charm et al., Enzyme inactivation with shearing. Biotechnol Bioeng. Nov. 1970;12(6):1103-9.

Newman et al., The Omron MicroAir vibrating mesh technology nebulizer, a 21$^{st}$ century approach to inhalation therapy. 2005, J Appl Ther Res. 5:29-33.

Niven et al., Some functional aspects of air-jet nebulizers. Int. J. Pharm. Apr. 1, 1994;104:73-85.

* cited by examiner

METHODS AND COMPOSITIONS FOR THE PREPARATION OF AEROSOLS

RELATED APPLICATIONS

This application is a continuation of U.S. application Ser. No. 13/577,961, filed Sep. 26, 2012 and now pending, which is a national stage filing under 35 U.S.C. § 371 of international application PCT/EP2011/052024, filed Feb. 11, 2011, which was published under PCT Article 21(2) in English, and claims the benefit under 35 U.S.C. § 119(e) of U.S. provisional application Ser. No. 61/303,447, filed Feb. 11, 2010, and of U.S. provisional application Ser. No. 61/426,610, filed Dec. 23, 2010, the disclosures of which are incorporated by reference herein in their entireties.

FIELD OF THE INVENTION

The present invention relates to methods for the preparation of an aerosol. More specifically the present invention provides methods for the preparation of an aerosol of immunoglobulin single variable domains wherein the amount of aggregate formation is significantly reduced. The invention further provides aerosols prepared by the methods of the invention, as well as compositions for use in the methods of the invention.

The invention further relates to methods for the preparations of such compositions, to containers, kits and aerosol delivery systems comprising such compositions and to uses of the same.

Other aspects, embodiments, advantages and applications of the invention will become clear from the further description herein.

BACKGROUND ART

Immunoglobulin single variable domains (as further described herein) are characterized by formation of the antigen binding site by a single variable domain, which does not require interaction with a further domain (e.g. in the form of VH/VL interaction) for antigen recognition. Immunoglobulin single variable domains against a wide range of different targets have been described (WO 04/062551, WO 05/044858, WO 06/040153, WO 06/122825, WO 07/104529, WO 08/020079, WO 08/074839, WO 08/071447, WO 08/074840, WO 08/074867, WO 08/077945, WO 08/101985, WO 08/142164, WO 09/068625, WO 08/142165, WO 09/068627) that could be candidates for drug development. Immunoglobulin single variable domains against the p19 subunit of IL-23 that block the interaction of IL-23 with its receptor have been described e.g. in WO 09/068627. Immunoglobulin single variable domains against the F protein of human Respiratory Syncytial Virus (hRSV) that can neutralize hRSV have been described e.g. in WO 09/147248.

Most immunoglobulin single variable domains in preclinical or clinical development have been administered parenterally (i.e. by intravenous or subcutaneous administration) and stable formulations for these administration methods have been described (see e.g. PCT application No. PCT/EP2010/062972 (filed 3 Sep. 2010) based on US provisional application No. U.S. 61/275,816 (filed 3 Sep. 2009) and PCT application No. PCT/EP2010/062975 (filed 3 Sep. 2010) based on US provisional application No. U.S. 61/284,502 filed by Ablynx N. V. on 18 Dec. 2009). These delivery methods, however, have a rather low patient acceptance and a need exists for alternative, more convenient (needle-free) modes of administration which can easily be performed by the patients themselves.

One possible alternative method is the delivery of the immunoglobulin single variable domain through the lungs. Pulmonary drug delivery can be achieved by inhalation, orally and/or nasally. Examples of pharmaceutical devices for pulmonary delivery include metered dose inhalers (MDIs), dry powder inhalers (DPIs), and nebulizers. Traditionally, nebulizers have been classified into two main types: air-jet (pneumatic) and ultrasonic devices. Recently, a third type, vibrating-mesh nebulizers has been commercialized (Newman and Gee-Turner, 2005, J. Appl. Ther. Res. 5: 29-33).

The nebulizer is a logical first choice for development of a pharmaceutical protein-based drug for pulmonary delivery as most proteins are purified and stored as aqueous concentrate. However, the stability of aqueous solutions on the shelf may not translate to stability during nebulization and the protein may be denatured by several mechanisms including drying, shear and surface effects (Charm and Wong, 1970, Biotechnol. Bioeng 12: 1103-1109; Andrews, 1991, Biochem. Soc. Trans, 272S 19). It was shown, for example, that nebulization induced the loss of enzymatic activity of lactate dehydrogenase (LDH) and resulted in aggregation, which mainly consisted of dimer formation, and degradation of recombinant human granulocyte stimulating factor (G-CSF) (Niven and Brain, 1994, Int. J. Pharm., 104: 73-85).

WO 04/041867 describes methods and compositions for the pulmonary delivery of immunoglobulin single variables domain. In WO 09/074634, methods of direct pulmonary delivery of domain antibodies, and particular domain antibody compositions suitable for direct pulmonary delivery, are described. More specifically, compositions are described which comprise a domain antibody polypeptide and a buffer containing 2% to about 10% PEG1000 and 1.2% sucrose (w/v). These domain antibody compositions appear to have a viscosity that allows the production of sufficient droplets with the correct size for administration to a subject by direct local pulmonary delivery. None of the above documents describe or discuss the reduction of aggregate formation and/or the improvement of the stability during pulmonary delivery of immunoglobulin single variable domains. There remains a need for additional methods and compositions for the delivery of intact and functional immunoglobulin single variable domains by the pulmonary route.

SUMMARY OF THE INVENTION

The present invention provides a method (also referred to as "method of the invention" or "methods of the invention") for the preparation of an aerosol (also referred to as "aerosol of the invention"; as further defined herein) of immunoglobulin single variable domains with low to undetectable levels of aggregation and/or without a significant loss of biological activity and/or potency of the immunoglobulin single variable domains. The method of the invention comprises the step of atomizing a composition (also referred to as "composition of the invention" or "compositions of the invention"; as further defined herein) comprising an aqueous carrier and a polypeptide (also referred to as "polypeptide of the invention" or "polypeptides of the invention"; as further defined herein) comprising one or more immunoglobulin single variable domains at a concentration of 1 mg/mL to 200 mg/mL. It has been demonstrated in the present invention that the presence of certain elements in the composition to be atomized ("composition of the invention") and/or the use of selected aerosol delivery systems significantly (and unexpectedly) reduces the amount of aggregate formation in the atomized material and, consequently, the loss of biological activity and/or potency of the polypeptides of the invention present in the atomized material. It has been shown that the amount of aggregate formation can be reduced to 7% or less, preferably 6% or less, 5% or less, such as 4% or less, 3% or less, 2% or less, or even 1% or less.

In one aspect, the presence of a detergent in the composition of the invention significantly reduced the amount of aggregate formation in the atomized material. Accordingly, the present invention relates to a method for the preparation of an aerosol of immunoglobulin single variable domains wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein the composition further comprises a surfactant at a concentration between 0.001% and 1% (v:v).

In a particular aspect, the presence of a detergent in the composition of the invention significantly reduced the amount of aggregate formation in the atomized material when the polypeptide of the invention was present in the composition of the invention at a concentration of lower than 20 mg/ml, such as e.g. at a concentration of 5 mg/ml, 10 mg/ml or 15 mg/ml. Accordingly, the present invention relates to a method for the preparation of an aerosol of immunoglobulin single variable domains wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, said method comprising the step of atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition further comprises a surfactant at a concentration between 0.001% and 1% (v:v).

Preferably the surfactant is present in the composition at a concentration between 0.001% and 0.1% (v:v), or between 0.01% and 0.1% (v:v) such as about 0.001% (v:v), 0.005% (v:v), 0.01% (v:v), 0.02% (v:v), 0.05% (v:v), 0.08% (v:v) or 0.1% (v:v), preferably about 0.04% to about 0.08% (v:v), in particular 0.04%. In a preferred aspect, the surfactant is selected from a non-ionic detergent, such as polysorbates (such as e.g. Tween 20, and Tween 80) and poloxamers (such as e.g. Pluronic®). In another aspect, polyethylene glycol (PEG) can be added as a surfactant-like compound. In yet another aspect, the composition comprises a surfactant as described above, which is not PEG. In particular, the composition does not comprise about 2% to about 10% PEG 1000 in 50 mM phosphate buffer containing 1.2% (w/v) sucrose). The reduction in aggregate formation was unexpected, particularly at such low concentrations of surfactant.

The presence of the polypeptide of the invention in the composition of the invention at a concentration of 20 mg/mL or more, such as e.g. at a concentration of 25 mg/mL or more, or at a concentration of 50 mg/ml or even more, also significantly reduced the amount of aggregate formation in the atomized material. Accordingly, in another aspect, the present invention relates to a method for the preparation of an aerosol of immunoglobulin single variable domains wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, said method comprising the step of atomizing a composition comprising an aqueous carrier and a polypeptide comprising one or more immunoglobulin single variable domains, wherein the polypeptide comprising one or more immunoglobulin single variable domains is present in the composition of the invention at a concentration of 20 mg/mL or more, such as e.g. at a concentration of 25 mg/mL or more, or at a concentration of 50 mg/ml or even more.

In a particular aspect, the presence of the polypeptide of the invention in the composition of the invention at a concentration of 20 mg/mL or more, such as e.g. at a concentration of 25 mg/mL or more, or at a concentration of 50 mg/ml or even more, significantly reduced the amount of aggregate formation in the atomized material in the absence of a surfactant. Accordingly, in yet another aspect, the present invention relates to a method for the preparation of an aerosol of immunoglobulin single variable domains wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the composition does not comprise a surfactant.

In a preferred aspect, the polypeptide comprising one or more immunoglobulin single variable domains is present in the composition at a concentration of 30 mg/mL, 40 mg/mL, 50 mg/mL, 60 mg/ml or more, 70 mg/ml or more, 80 mg/ml or even more. In a most preferred aspect, the polypeptide comprising one or more immunoglobulin single variable domains is present in the composition at a concentration of 50 mg/mL. The reduction in aggregate formation at higher concentrations (e.g., an inverse relationship between concentration and aggregate formation), such as at a concentration of 20 mg/mL or more, e.g. at a concentration of 25 mg/mL or more, or at a concentration of 50 mg/ml or even more, was unexpected.

The use of a particular aerosol delivery system, i.e. the vibrating-mesh or vibrating-membrane nebulizer, for atomizing the composition of the invention also significantly reduced the amount of aggregate formation in the atomized material. Accordingly, in yet another aspect, the present invention relates to a method for the preparation of an aerosol of immunoglobulin single variable domains wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein the composition is atomized in a vibrating-mesh nebulizer. The reduction in aggregate formation using a vibrating-mesh or vibrating-membrane nebulizer was unexpected.

The method of the invention preferably is capable of producing an aerosol that has a volume median diameter between 1 and 10 µm, preferably between 1 and 7 µm, most preferably between 1 and 5 µm, such as around 3, 3.5 or 4 µm.

The present invention also relates to an aerosol ("aerosol of the invention") prepared by the method of the invention. The aerosol preferably has a volume median diameter between 1 and 10 µm, preferably between 1 and 7 µm, most preferably between 1 and 5 µm, such as around 3, 3.5 or 4 µm. Accordingly, in one aspect, the present invention relates to an aerosol comprising liquid droplets obtainable by atomizing a composition comprising an aqueous carrier and a polypeptide comprising one or more immunoglobulin single variable domains at a concentration of 1 mg/mL to 200 mg/mL, wherein the amount of aggregate formation in the atomized material is 7% or lower, preferably 6% or lower, 5% or lower, such as 4% or lower, 3% or lower, 2% or lower, or even 1% or lower, the % of aggregate formation as determined by SE-HPLC, and wherein the composition further comprises a surfactant at a concentration between 0.001% and 1% (v:v).

In a particular aspect, the present invention relates to an aerosol comprising liquid droplets obtainable by atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the amount of aggregate formation in the atomized material is 7% or lower, preferably 6% or lower, 5% or lower, such as 4% or lower, 3% or lower, 2% or lower, or even 1% or lower, the % of aggregate formation as determined by SE-HPLC, and wherein the composition further comprises a surfactant at a concentration between 0.001% and 1% (v:v).

Preferably the surfactant is present in the composition at a concentration between 0.001% and 0.1% (v:v), or between 0.01% and 0.1% (v:v) such as about 0.001% (v:v), 0.005% (v:v), 0.01% (v:v), 0.02% (v:v), 0.05% (v:v), 0.08% (v:v) or 0.1% (v:v), preferably about 0.04% to about 0.08% (v:v), in particular 0.04%. In a preferred aspect, the surfactant is selected from a non-ionic detergent, such as polysorbates (such as e.g. Tween 20, and Tween 80) and poloxamers. In another aspect, PEG can be added as a surfactant-like compound. In another aspect, the surfactant is not PEG. In particular, the composition does not comprise about 2% to about 10% PEG 1000 in 50 mM phosphate buffer containing 1.2% (w/v) sucrose).

In another aspect, the invention also relates to an aerosol comprising liquid droplets obtainable by atomizing a composition comprising an aqueous carrier and a polypeptide comprising one or more immunoglobulin single variable domains, wherein the amount of aggregate formation in the atomized material is 7% or lower, preferably 6% or lower, 5% or lower, such as 4% or lower, 3% or lower, 2% or lower, or even 1% or lower, the % of aggregate formation as determined by SE-HPLC, and wherein the polypeptide comprising one or more immunoglobulin single variable domains is present in the composition at a concentration of 20 mg/mL or more, such as e.g. at a concentration of 25 mg/mL or more, or at a concentration of 50 mg/ml or even more.

In yet another aspect, the invention relates to an aerosol comprising liquid droplets obtainable by atomizing a composition comprising an aqueous carrier and a polypeptide comprising one or more immunoglobulin single variable domains, wherein the amount of aggregate formation in the atomized material is 7% or lower, preferably 6% or lower, 5% or lower, such as 4% or lower, 3% or lower, 2% or lower, or even 1% or lower, the % of aggregate formation as determined by SE-HPLC, wherein the polypeptide comprising one or more immunoglobulin single variable domains is present in the composition at a concentration of 20 mg/mL or more, such as e.g. at a concentration of 25 mg/mL or more, or at a concentration of 50 mg/ml or even more, and wherein the composition does not comprise a surfactant.

In a preferred aspect, the polypeptide comprising one or more immunoglobulin single variable domains is present in the composition at a concentration of 30 mg/mL, 40 mg/mL, 50 mg/mL, 60 mg/ml or more, 70 mg/ml or more, 80 mg/ml, or even more. In a most preferred aspect, the polypeptide comprising one or more immunoglobulin single variable domains is present in the composition at a concentration of 50 mg/ml.

In yet another aspect, the invention relates to an aerosol comprising liquid droplets obtainable by atomizing a composition comprising an aqueous carrier and a polypeptide comprising one or more immunoglobulin single variable domains at a concentration of 1 mg/mL to 200 mg/mL, wherein the amount of aggregate formation is 7% or lower, preferably 6% or lower, 5% or lower, such as 4% or lower, 3% or lower, 2% or lower, or even 1% or lower, the % of aggregate formation as determined by SE-HPLC, wherein the composition is atomized in a vibrating-mesh nebulizer.

The invention also relates to a composition ("composition of the invention" or "compositions of the invention") suitable for use in the method of the invention and/or suitable for the preparation of the aerosol of the invention. Accordingly, in one aspect, the present invention relates to a composition suitable for the preparation of an aerosol of immunoglobulin single variable domains with an amount of aggregate formation of 7% or lower, preferably 6% or lower, 5% or lower, such as 4% or lower, 3% or lower, 2% or lower, or even 1% or lower, the % of aggregate formation as determined by SE-HPLC, said composition comprising an aqueous carrier and a polypeptide comprising one or more immunoglobulin single variable domains at a concentration of 1 mg/mL to 200 mg/mL, wherein the composition further comprises a surfactant at a concentration between 0.001% and 1% (v:v).

In a particular aspect, the present invention relates to a composition suitable for the preparation of an aerosol of immunoglobulin single variable domains with an amount of aggregate formation of 7% or lower, preferably 6% or lower, 5% or lower, such as 4% or lower, 3% or lower, 2% or lower, or even 1% or lower, the % of aggregate formation as determined by SE-HPLC, said composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition further comprises a surfactant at a concentration between 0.001% and 1% (v:v).

Preferably the surfactant is present in the composition at a concentration between 0.001% and 0.1% (v:v), or between 0.01% and 0.1% (v:v) such as about 0.001% (v:v), 0.005% (v:v), 0.01% (v:v), 0.02% (v:v), 0.05% (v:v), 0.08% (v:v) or 0.1% (v:v), preferably about 0.04% to about 0.08% (v:v), in particular 0.04%. In a preferred aspect, the surfactant is selected from a non-ionic detergent, such as polysorbates (such as e.g. Tween 20, and Tween 80) and poloxamers. In another aspect, PEG can be added as a surfactant-like compound. In yet another aspect, the surfactant is not PEG. In particular, the composition does not comprise about 2% to about 10% PEG 1000 in 50 mM phosphate buffer containing 1.2% (w/v) sucrose).

In another aspect, the present invention relates to a composition suitable for the preparation of an aerosol of immunoglobulin single variable domains in which the amount of aggregate formation is 7% or lower, preferably 6% or lower, 5% or lower, such as 4% or lower, 3% or lower, 2% or lower, or even 1% or lower, the % of aggregate formation as determined by SE-HPLC, said composition comprising an aqueous carrier and a polypeptide comprising one or more immunoglobulin single variable domains, wherein the polypeptide comprising one or more immunoglobulin single variable domains is present in the composition at a concentration of 20 mg/mL or more, such as e.g. at a concentration of 25 mg/mL or more, or at a concentration of 50 mg/ml or even more.

In yet another aspect, the invention relates to a composition suitable for the preparation of an aerosol of immunoglobulin single variable domains in which the amount of aggregate formation is 7% or lower, preferably 6% or lower, 5% or lower, such as 4% or lower, 3% or lower, 2% or lower, or even 1% or lower, the % of aggregate formation as determined by SE-HPLC, wherein the polypeptide comprising one or more immunoglobulin single variable domains is present in the composition at a concentration of 20 mg/mL or more, such as e.g. at a concentration of 25 mg/mL or more, or at a concentration of 50 mg/ml or even more, and wherein the composition does not comprise a surfactant.

In a preferred aspect, the polypeptide comprising one or more immunoglobulin single variable domains is present in the composition at a concentration of 30 mg/mL, 40 mg/mL, 50 mg/mL, 60 mg/ml or more, 70 mg/ml or more, 80 mg/ml or even more. In a most preferred aspect, the polypeptide comprising one or more immunoglobulin single variable domains is present in the composition at a concentration of 50 mg/ml.

The polypeptide (also referred to as "polypeptide of the invention" or "polypeptides of the invention") comprises or essentially consists of one or more immunoglobulin single variable domain (as defined herein). In one aspect, the polypeptide of the invention comprises or essentially consists of one immunoglobulin single variable domain. In another aspect, the polypeptide of the invention comprises or essentially consists of two or more immunoglobulin single variable domains, such as two or three. In another aspect, the polypeptide of the invention specifically binds hRSV or IL-23. In another aspect, the polypeptide of the invention is selected from one of SEQ ID NO's: 1, 2 and 3. The invention also relates to methods for the preparation of the composition of the invention.

The methods at least comprise the step of concentrating the polypeptide and exchanging it with the selected buffer. In one aspect, the method for the preparation of a composition of the invention additionally comprises the step of adding a surfactant at a concentration between 0.001% and 1% (v:v).

In a particular aspect, the method for the preparation of a composition of the invention comprise the step of concentrating the polypeptide to a concentration of lower than 20 mg/ml, such as e.g. at a concentration of 5 mg/ml, 10 mg/ml or 15 mg/ml, and additionally comprises the step of adding a surfactant at a concentration between 0.001% and 1% (v:v).

Preferably the surfactant is added at a concentration between 0.001% and 0.1% (v:v), or between 0.01% and 0.1% (v:v) such as about 0.001% (v:v), 0.005% (v:v), 0.01% (v:v), 0.02% (v:v), 0.04% (v:v), 0.05% (v:v), 0.08% (v:v) or 0.1% (v:v), preferably about 0.04% to about 0.08% (v:v), in particular 0.04%. In a preferred aspect, the surfactant is selected from a non-ionic detergent, such as polysorbates (such as e.g. Tween 20, and Tween 80) and poloxamers. In another aspect, PEG can be added as a surfactant-like compound. In yet another aspect, the surfactant is not PEG. In particular, the composition does not comprise about 2% to about 10% PEG 1000 in 50 mM phosphate buffer containing 1.2% (w/v) sucrose).

In another aspect, in the method for the preparation of a composition of the invention the polypeptide is concentrated to a concentration of 20 mg/mL or more, such as e.g. at a concentration of 25 mg/mL or more, or at a concentration of 50 mg/ml or even more.

In yet another aspect, in the method for the preparation of a composition of the invention the polypeptide is concentrated to a concentration of 20 mg/mL or more, such as e.g. at a concentration of 25 mg/mL or more, or at a concentration of 50 mg/ml or even more, and no surfactant is added.

In a preferred aspect, the polypeptide is concentrated to a concentration of 30 mg/mL, 40 mg/mL, 50 mg/mL, 60 mg/ml or more, 70 mg/ml or more, 80 mg/ml, or even more. In a most preferred aspect, the polypeptide comprising one or more immunoglobulin single variable domains is present in the composition at a concentration of 50 mg/ml.

The invention further provides for the use of the methods, aerosol and compositions of the invention. The methods, aerosol and compositions of the invention can be used for the preparation of a medicament for delivery to a human subject by an aerosol delivery system. Preferably the medicament is delivered by nebulisation, such as through a vibrating-mesh nebulizer. Also provided are aerosol delivery systems. The aerosol delivery system should at least comprise a container and an aerosol generator connected to the container, wherein the container comprises a composition of the invention. The aerosol delivery system may be a nebulizer. In one aspect of the invention, the aerosol delivery system is a vibrating-mesh nebulizer.

Further provided are containers, kits and pharmaceutical unit dosages comprising the compositions of the invention for use by, e.g., a healthcare professional. The containers, kits or pharmaceutical unit dosages comprising the compositions of the invention should be suitable for pulmonary administration of the polypeptide of the invention to a human subject. Preferably the containers, kits or pharmaceutical unit dosages comprising the compositions of the invention should be suitable for administration of the polypeptide of the invention to a human subject by an aerosol delivery system such as e.g. a nebulizer. In one aspect of the invention, the nebulizer is a vibrating-mesh nebulizer.

The compositions, containers, aerosol delivery systems, nebulizers, pharmaceutical unit dosages and/or kits can be used in prophylaxis and/or therapy. In a specific aspect, the compositions, containers, aerosol delivery systems, nebulizers, pharmaceutical unit dosages and/or kits are used for the prevention and/or treatment of one or more diseases and/or disorders such as respiratory diseases and/or disorders (e.g. hRSV infection). Accordingly, the present invention also relates to a method for prevention and/or treatment of one or more diseases and/or disorders, such as one or more respiratory diseases, said method comprising the step of administering to a subject in need thereof, through an aerosol delivery system, a composition of the invention. In one aspect, the disease and/or disorder treated is hRSV infection. In another aspect the composition is administered through a nebulizer, such as a vibrating-mesh nebulizer.

The present invention also relates to the use of a composition, container, kit, pharmaceutical unit dosages, aerosol delivery system and/or nebulizer for the preparation of a medicament for prevention and/or treatment of respiratory diseases (e.g. hRSV infection).

Figure 1:
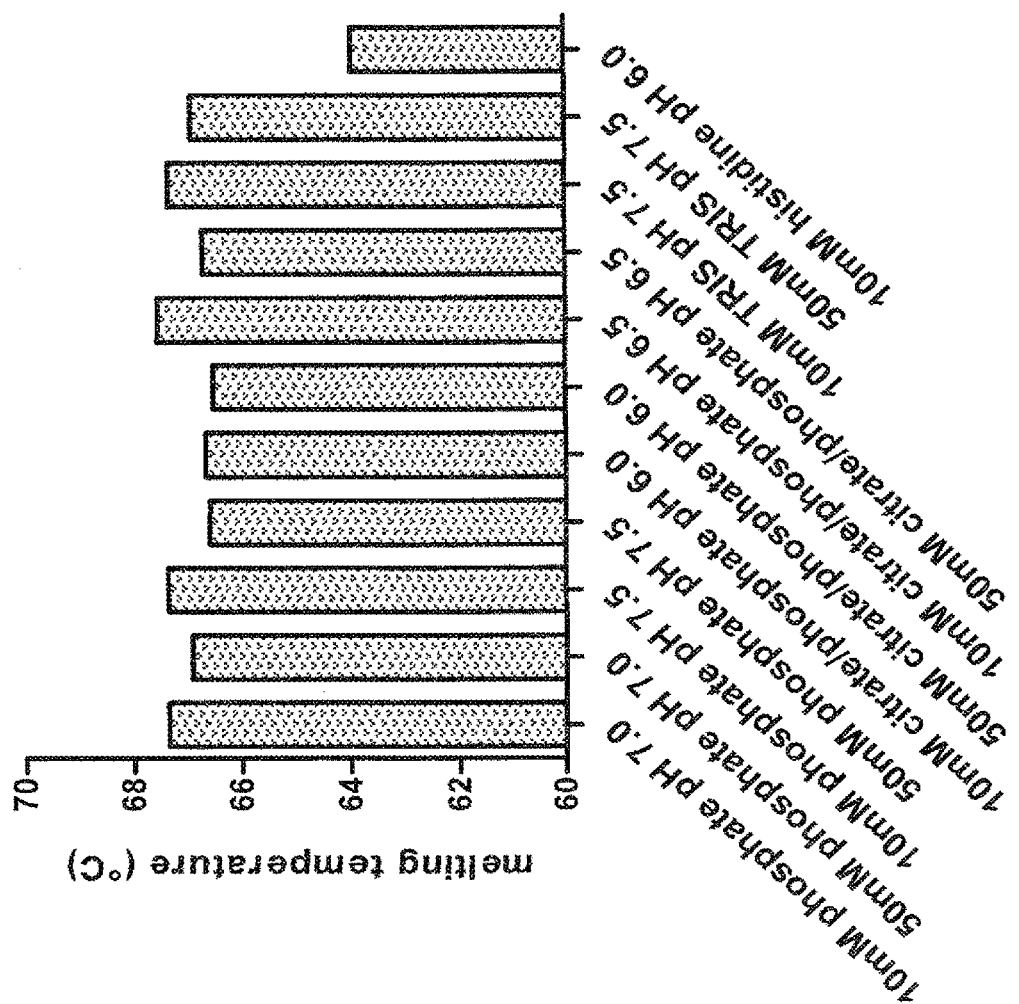
FIG. 1. Comparison of melting temperatures (Tm) of RSV434 in the presence of different buffering agents with mannitol as osmolarity agent. Measurements were performed via thermal shift assay (TSA) at 0.1 mg/mL.

As used herein, the term "effective amount" refers to the amount of an agent (e.g. a prophylactic or therapeutic agent) which is sufficient to reduce and/or ameliorate the severity and/or duration of one or more diseases and/or disorders.

As used herein, the terms "therapeutic agent" and "therapeutic agents" refer to any agent(s) which can be used in the prevention, treatment and/or management of one or more diseases and/or disorders. In the context of the present invention, the term "therapeutic agent" refers to a polypeptide comprising one or more immunoglobulin single variable domains. In certain other embodiments, the term "therapeutic agent" refers to an agent other than the polypeptide of the invention which might be used in the composition.

As used herein, the term "therapeutically effective amount" refers to the amount of a therapeutic agent (e.g. a polypeptide comprising one or more immunoglobulin single variable domains), that is sufficient to reduce the severity of one or more diseases and/or disorders.

The term "excipient" as used herein refers to an inert substance which is commonly used as a diluent, vehicle, preservative, binder or stabilizing agent for drugs which imparts a beneficial physical property to a formulation, such as increased protein stability, increased protein solubility, and/or decreased viscosity. Examples of excipients include, but are not limited to, proteins (e.g., serum albumin), amino acids (e.g., aspartic acid, glutamic acid, lysine, arginine, glycine), surfactants (e.g., sodium dodecyl sulfate (SDS), polysorbates such as Tween 20 and Tween 80, poloxamers such as Pluronics, and other nonionic surfactants such as poly(ethylene glycol) (PEG)), saccharides (e.g., glucose, sucrose, maltose and trehalose), polyols (e.g., mannitol and sorbitol), fatty acids and phospholipids (e.g., alkyl sulfonates and caprylate). For additional information regarding excipients, see Remington's Pharmaceutical Sciences (by Joseph P. Remington, 18th ed., Mack Publishing Co., Easton, Pa.), which is incorporated herein in its entirety.

The term "variable domain" refers to the part or domain of an immunoglobulin molecule or antibody which is partially or fully responsible for antigen binding. The term "single variable domain", defines molecules wherein the antigen binding site is present on, and formed by, a single immunoglobulin domain. This sets single variable domains apart from "conventional" immunoglobulins or their fragments, wherein two immunoglobulin domains, in particular two "variable domains" interact to form an antigen binding site. Typically, in conventional immunoglobulins, a heavy chain variable domain (VH) and a light chain variable domain (VL) interact to form an antigen binding site. In this case, the complementarity determining regions (CDRs) of both VH and VL will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs. The term "immunoglobulin single variable domain" does comprise fragments of conventional immunoglobulins wherein the antigen binding site is formed by a single variable domain.

Generally, immunoglobulin single variable domains will be amino acid sequences that essentially consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such immunoglobulin single variable domains and fragments are most preferably such that they comprise an immunoglobulin fold or are capable for forming, under suitable conditions, an immunoglobulin fold. As such, the immunoglobulin single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that essentially consists of the immunoglobulin single variable domain, such that the single antigen binding domain does not need to interact with another variable domain to form a functional antigen binding unit, as is for example the case for the variable domains that are present in for example conventional antibodies and scFv fragments that need to interact with another variable domain—e.g. through a $V_H/V_L$ interaction—to form a functional antigen binding domain).

In one aspect of the invention, the immunoglobulin single variable domains are light chain variable domain sequences (e.g. a $V_L$-sequence), or heavy chain variable domain sequences (e.g. a $V_H$-sequence); more specifically, the single variable domains can be heavy chain variable domain sequences that are derived from a conventional four-chain antibody or heavy chain variable domain sequences that are derived from a heavy chain antibody.

The immunoglobulin single variable domain may be a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N. V.]; other immunoglobulin single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341: 544-546), to Holt et al. 2003 (Trends Biotechnol. 21: 484-490); as well as to for example WO 04/068820, WO 06/030220, WO 06/003388 and other published patent applications of Domantis Ltd. It should also be noted that, although less preferred in the context of the present invention because they are not of mammalian origin, immunoglobulin single variable domains can be derived from certain species of shark (for example, the so-called "IgNAR domains", see for example WO 05/18629).

In particular, the polypeptides of the invention may comprise one or more Nanobodies or a suitable fragment thereof. For a further description of $V_{HH}$'s and Nanobodies, reference is made to the review article by Muyldermans 2001 (Reviews in Molecular Biotechnology 74: 277-302; as well as to the following patent applications, which are mentioned as general background art: WO 94/04678, WO9504079 and WO9634103 of the Vrije Universiteit Brussel; WO9425591, WO9937681, WO0040968, WO0043507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N. V. and Ablynx N. V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N. V. and the further published patent applications by Ablynx N. V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101985 and WO 08/142164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "immunoglobulin single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

The term "immunoglobulin single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann (1994, FEBS Lett. 339: 285-290) and (1996, Protein Eng. 9: 531-537)). Moreover, the invention comprises fused variable domains, e.g. multivalent and/or multispecific constructs (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

The immunoglobulin single variable domains provided by the invention are preferably in essentially isolated form (as defined herein), or form part of a polypeptide (also referred to as "polypeptide of the invention"), which may comprise or essentially consist of one or more immunoglobulin single variable domains and which may optionally further comprise one or further amino acid sequences (all optionally linked via one or more suitable linkers). For example, and without limitation, the one or more immunoglobulin single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101985, WO 08/142164, WO 09/068625, WO 09/068627 and WO 08/020079. Such a protein or polypeptide may also be in essentially isolated form (as defined herein) and the methods, aerosols and compositions of the present invention equally apply to immunoglobulin single variable domains and to polypeptides comprising one or more immunoglobulin single variable domains.

According to the invention, the term "immunoglobulin single variable domain" may comprise constructs comprising two or more antigen binding units in the form of immunoglobulin single variable domain, as outlined above. For example, two (or more) immunoglobulin single variable domains with the same or different antigen specificity can be linked to form e.g. a bivalent, trivalent or multivalent construct. By combining immunoglobulin single variable domains of two or more specificities, bispecific, trispecific etc. constructs can be formed. For example, an immunoglobulin single variable domain according to the invention may comprise or essentially consist of two or three identical immunoglobulin single variable domains, or two immunoglobulin single variable domains directed against target A, and one immunoglobulin single variable domain against target B. Such constructs and modifications thereof, which the skilled person can readily envisage, are all encompassed by the term "immunoglobulin single variable domain" as used herein and are also referred to as "polypeptide of the invention" or "polypeptides of the invention".

As further described in paragraph m) on page 53 of WO 08/020079, an amino acid sequence (such as a Nanobody, an antibody, a polypeptide of the invention, or generally an antigen binding protein or polypeptide or a fragment thereof) that can (specifically) bind to, that has affinity for and/or that has specificity for a specific antigenic determinant, epitope, antigen or protein (or for at least one part, fragment or epitope thereof) is said to be "against" or "directed against" said antigenic determinant, epitope, antigen or protein.

An "aerosol" as used herein refers to a suspension of liquid in the form of fine particles dispersed in a gas (i.e. a fine mist or spray containing minute particles). As used herein, the term "particle" refers to liquids, e.g., droplets. Pharmaceutical aerosols for the delivery of the polypeptides of the invention to the lungs can be inhaled via the mouth and/or via the nose. In pulmonary delivery, the generation of particles smaller than approximately 5 or 6 micrometer is considered necessary to achieve deposition as the fine particle fraction (FPF) (i.e. in the respiratory bronchioles and alveolar region) (O'Callaghan and Barry, 1997, Thorax 52: S31-S44). The particle size in an aerosol can be expressed as volume median diameter (VMD). The "volume median diameter" is defined as the geometric particle diameter of an aerosol, where 50% of the aerosol volume is larger than this value and 50% is smaller than this value. "Mass median aerodynamic diameter (MMAD)" is defined as the geometric mean aerodynamic diameter, where 50% of the particles by weight will be smaller than this value and 50% will be larger than this value. When the density of the aerosol particles is 1 g/cm3, the VMD and MMAD are equivalent. The aerosol of the present invention preferably has a volume median diameter between 1 and 10 µm, preferably between 1 and 7 µm, most preferably between 1 and 5 µm, such as around 3, 3.5 or 4 µm.

"Aerosolization" as used in the present invention means the production of an aerosol by the transformation of a composition of the invention into small particles or droplets. This is usually done through an aerosol delivery system (as further defined).

In the context of the present invention, the term "atomize" and "atomization" means the production of droplets by (mechanical) disruption of a bulk liquid. The produced droplets will make up the fine mist or spray that forms the aerosol.

The terms "nebulizer" and "nebulization" as used in the present invention refers to the conversion of a liquid into a mist or fine spray by a nebulizer (as further defined herein).

The terms "atomized material" or "aerosolized material" is the material (such as the composition comprising one or more immunoglobulin single variable domains) that has gone through the process of aerosolization. This material can still be in the form of an aerosol (as defined herein). It can also be that this material has transformed back to a bulk liquid that has been collected by combining the different droplets present in the aerosol.

The terms "stability" and "stable" as used herein refer to the resistance to aggregation of the polypeptide of the invention comprising one or more immunoglobulin single variable domains upon atomization of the composition comprising said polypeptide. Apart from this and/or in addition, the "stable" compositions of the invention retain biological activity upon atomization. The stability of said polypeptide can be assessed by degrees of aggregation, as measured e.g. by SE-HPLC, subvisible particle counting, analytical ultracentrifugation, dynamic light scattering, OD320/OD280 ratio measurement, elastic light scattering, etc., and/or by % of biological activity (as measured e.g. by ELISA, Biacore, etc.) compared to a reference compositions which has not been atomized.

"Aggregation" or "aggregate formation" as used in the present invention means the development of aggregates. In the context of the present invention, an "aggregate" includes any particle which consists of more than one identical subunit (or monomer) of the polypeptide of the invention, also including oligomers, such as e.g. dimers, trimers, tetramers, pentamers and the like. The aggregates can be of different sizes, including high molecular weight aggregates, as well as low molecular weight aggregates. As used herein, high molecular weight (abbreviated as HMW) aggregates usually consist of more than four monomer units, such as pentamers; low molecular weight aggregates usually consist of four or less monomer units, such as dimers, trimers and/or tetramers.

The phrase "low to undetectable levels of aggregation" as used herein refers to samples containing no more than 7%, no more than 6%, no more than 5%, no more than 4%, no more than 3%, no more than 2%, no more than 1%, or no more than 0.5% aggregation by weight of protein.

In the methods, aerosols and compositions of the invention, less than 7% (more preferably less than 6%, less than 5%, even more preferably less than 4%, less than 3%, less than 2%, or most preferably less than 1%) of the polypeptide of the invention forms aggregates (as defined herein) during atomization. Aggregate formation in the atomized material can be assessed by various analytical and/or immunological methods known in the art including but not limited to e.g. size exclusion chromatography (SE-HPLC), subvisible particle counting, analytical ultracentrifugation (AUC), dynamic light scattering (DLS), static light scattering (SLS), elastic light scattering, OD320/OD280, Fourier Transform Infrared Spectroscopy (FTIR), circular dichroism (CD), urea-induced protein unfolding techniques, intrinsic tryptophan fluorescence and/or differential scanning calorimetry techniques. The molecular size distribution and the relative amounts of polypeptide of the invention and protein impurities can be determined by Size Exclusion High Performance Liquid Chromatography (SE-HPLC). SE-HPLC methods are known to the skilled person and are also described in the Example section.

In an analytical ultracentrifuge, a sample being spun can be monitored in real time through an optical detection system, using ultraviolet light absorption and/or interference optical refractive index sensitive system. This allows the operator to observe the evolution of the sample concentration versus the axis of rotation profile as a result of the applied centrifugal field. With modern instrumentation, these observations are electronically digitized and stored for further mathematical analysis. Two kinds of experiments are commonly performed on these instruments: sedimentation velocity experiments and sedimentation equilibrium experiments.

Sedimentation velocity experiments aim to interpret the entire time-course of sedimentation, and report on the shape and molar mass of the dissolved macromolecules, as well as their size-distribution (Perez-Ramirez and Steckert, 2005, Therapeutic Proteins: Methods and Protocols. C. M. Smales and D. C. James, Eds. Vol. 308: 301-318. Humana Press Inc, Totowa, N.J., US). The size resolution of this method scales approximately with the square of the particle radii, and by adjusting the rotor speed of the experiment size-ranges from 100 Da to 10 GDa can be covered. Sedimentation velocity experiments can also be used to study reversible chemical equilibria between macromolecular species, by either monitoring the number and molar mass of macromolecular complexes, by gaining information about the complex composition from multi-signal analysis exploiting differences in each components spectroscopic signal, or by following the composition dependence of the sedimentation rates of the macromolecular system, as described in Gilbert-Jenkins theory.

Sedimentation equilibrium experiments are concerned only with the final steady-state of the experiment, where sedimentation is balanced by diffusion opposing the concentration gradients, resulting in a time-independent concentration profile. Sedimentation equilibrium distributions in the centrifugal field are characterized by Boltzmann distributions. This experiment is insensitive to the shape of the macromolecule, and directly reports on the molar mass of the macromolecules and, for chemically reacting mixtures, on chemical equilibrium constants.

The kinds of information that can be obtained from an analytical ultracentrifuge include the gross shape of macromolecules, the conformational changes in macromolecules, and size distributions of macromolecular samples. For macromolecules, such as proteins, that exist in chemical equilibrium with different non-covalent complexes, the number and subunit stoichiometry of the complexes and equilibrium constants can be studied. (see also Scott D. J., Harding S. E. and Rowe A. J. Analytical Ultracentrifugation Techniques and Methods, RSC Publishing).

Dynamic light scattering (also known as Photon Correlation Spectroscopy or quasi-elastic light scattering) is a technique in physics, which can be used to determine the size distribution profile of small particles in solution. When a beam of light passes through a colloidal dispersion, the particles or droplets scatter some of the light in all directions. When the particles are very small compared with the wavelength of the light, the intensity of the scattered light is uniform in all directions (Rayleigh scattering); for larger particles (above approximately 250 nm diameter), the intensity is angle dependent (Mie scattering). If the light is coherent and monochromatic, as from a laser for example, it is possible to observe time-dependent fluctuations in the scattered intensity using a suitable detector such as a photomultiplier capable of operating in photon counting mode.

These fluctuations arise from the fact that the particles are small enough to undergo random thermal (Brownian) motion and the distance between them is therefore constantly varying. Constructive and destructive interference of light scattered by neighbouring particles within the illuminated zone gives rise to the intensity fluctuation at the detector plane which, as it arises from particle motion, contains information about this motion. Analysis of the time dependence of the intensity fluctuation can therefore yield the diffusion coefficient of the particles from which, via the Stokes Einstein equation, knowing the viscosity of the medium, the hydrodynamic radius or diameter of the particles can be calculated. (see also Berne B. J. and Pecora R. Dynamic Light Scattering With Applications to Chemistry, Biology and Physics, Dover Publications).

Aggregation can also be measured by the PAMAS SVSS-C (Small Volume Syringe System-C) instrument (PArtikelMess-und AnalyseSysteme GMBH), which is a particle size distribution analyzer for low viscous fluids. It uses the principle of light obscuration to detect sub-visible particles in the size range 1 μm-200 μm. The validation criteria/specified limits of the European Pharmacopoeia (EP<2.9.19 Particulate Contamination: sub-visible particles) for small and large volume parenterals are defined by the total counts per container:

For particles >10 μm, no more than 6000 counts per container

For particles >25 μm, no more than 600 counts per container

The OD320/OD280 ratio is also a measure for turbidity or the presence of particulates in the sample. In a preferred aspect, the OD320/OD280 ratio of the composition of the invention should be 0.05 or lower, preferably 0.01 or lower, such as 0.005 or lower.

The tendency for aggregate formation of a polypeptide in a certain aerosol can also be measured by elastic light scattering. Elastic light scattering can be measured in a spectrofluorometer (e.g. excitation and emission wavelength 500 nm) by temperature-induced denaturation as measured e.g. at an angle of 90°. Preferably the maximum scatter will stay within the absorption detection limit. The scatter should be 1000 abs. or lower, preferably 750 abs or lower, such as 500 abs or lower.

The protein content of the recovered polypeptides of the invention in the atomized material can, for example, be detected by SE-HPLC or by spectrophotometrical methods.

A significantly reduced aggregate formation of the polypeptides of the invention has been observed upon atomization of compositions additionally comprising a surfactant at a concentration between 0.001% and 1% (v:v); upon atomization of compositions that contain the polypeptide of the invention at a concentration of 20 mg/mL or more, such as e.g. at a concentration of 25 mg/mL or more, or at a concentration of 50 mg/ml or even more; and/or when a vibrating-mesh nebulizer was used for atomization of the composition.

Accordingly, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein:

the composition further comprises a surfactant at a concentration between 0.001% and 1% (v:v);

the polypeptide comprising one or more immunoglobulin single variable domains is present in the composition at a concentration of 20 mg/mL or more; and/or the composition is atomized in a vibrating-mesh nebulizer.

In one aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein the composition further comprises a surfactant at a concentration between 0.001% and 1% (v:v); and/or the composition is atomized in a vibrating-mesh nebulizer.

In another aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition further comprises a surfactant at a concentration between 0.001% and 1% (v:v); and/or the composition is atomized in a vibrating-mesh nebulizer.

In yet another aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, and/or the composition is atomized in a vibrating-mesh nebulizer.

In still another aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the composition does not comprise a surfactant; and/or the composition is atomized in a vibrating-mesh nebulizer.

Apart from this and/or in addition, in the methods, aerosols and compositions of the invention, little to no loss of potency and/or biological activity of the polypeptides of the invention in the atomized material has been observed.

The potency and/or biological activity of a biological describes the specific ability or capacity of said biological to achieve a defined biological effect. The terms "biological activity" or "biological activities" as used herein refers to immunoglobulin single variable domain activities, including but not limited to, specific binding abilities of the immunoglobulin single variable domain to the target of interest as measured by various immunological assays, including, but not limited to ELISAs and/or by Surface Plasmon Resonance (Biacore). In one embodiment, upon atomization of the composition of the invention, the immunoglobulin single variable domains present in the atomized material retain at least 50%, preferably at least 55%, 60%, 65%, 70%, 75%, 80%, 85%, 90%, 95%, 98% or even 99% or more of the ability to specifically bind to the target of interest as compared to a reference composition (which has not been atomized), as measured by an immunological assay known to one of skill in the art or described herein. For example, an ELISA based assay may be used to compare the abilities of the immunoglobulin single variable domain to specifically bind to its target after atomization of said immunoglobulin single variable domain and without atomization of said immunoglobulin single variable domain.

The potency and biological activities of the polypeptides of the invention can be assessed by various assays including any suitable in vitro assay, cell-based assay, in vivo assay and/or animal model known per se, or any combination thereof, depending on the specific disease or disorder involved. Suitable in vitro assays will be clear to the skilled person, and for example include ELISA; FACS binding assay; Biacore; competition binding assay (AlphaScreen®, Perkin Elmer, Massachusetts, USA; FMAT). For example, SEQ ID NO: 2 and 3 interact with the F protein of hRSV and blocks the interaction of the F protein with its receptor. SEQ ID NO: 1 interacts with IL-23 and blocks the interaction of this ligand with its receptor. The potency of SEQ ID NO's: 1, 2 and 3 for blocking the respective ligand/receptor interaction can be determined, e.g. by ELISA, Biacore, AlphaScreen®.

For example, in one embodiment, Biacore kinetic analysis uses Surface Plasmon Resonance (SPR) technology to monitor macromolecular interactions in real time and is used to determine the binding on and off rates of polypeptides of the composition of the invention to their target. Biacore kinetic analysis comprises analyzing the binding and dissociation of the target from chips with immobilized polypeptides of the invention on their surface. A typical Biacore kinetic study involves the injection of 250 µL of polypeptide reagent at varying concentration in HEPES-buffered saline (HBS) buffer containing 0.005% Tween 20 over a sensor chip surface, onto which has been immobilized the antigen. In the BIAcore 3000 system, the ligand is immobilized on carboxymethylated dextran over a gold surface, while the second partner (analyte) is captured as it flows over the immobilized ligand surface. The immobilized ligands are remarkably resilient and maintain their biological activity. The bound analytes can be stripped from the immobilized ligand without affecting its activity to allow many cycles of binding and regeneration on the same immobilized surface. Interaction is detected in real time via SPR and at high sensitivity. Because the same affinity may reflect different on-rates and off-rates, this instrument excels over most other affinity measuring methods in that it measures on-rates (ka) and off-rates (kd). Concentration determination experiments are also feasible.

In the methods, aerosols and compositions of the invention, little to no loss of potency and/or biological activity of the polypeptides of the invention in the atomized material has been observed, as assessed by various immunological assays including, for example, enzyme-linked immunosorbent assay (ELISA) and Surface Plasmon Resonance, measuring the ability of the polypeptide to specifically bind to its antigen. Upon atomization, the polypeptides present in the composition of the present invention retain more than 80%, more than 85%, more than 90%, more than 95%, more than 98%, more than 99%, or even more than 99.5% of their initial biological activities (e.g., the ability to bind to IL-23, hRSV) of the polypeptides prior to atomization.

In a specific embodiment of the invention, the polypeptides bind IL-23. Upon atomization of the composition of the present invention comprising said IL-23 binding polypeptides, at least 80% (at least 85%, at least 90%, at least 95%, at least 98%, at least 99%, or at least 99.5%) of the polypeptides retain their binding activity to IL-23.

In another specific embodiment, the polypeptides bind hRSV. Upon atomization of the composition of the present invention comprising said hRSV binding polypeptides, at least 80% (at least 85%, at least 90%, at least 95%, at least 98%, at least 99%, or at least 99.5%) of the polypeptides of the invention retain their binding activity to hRSV.

Other suitable in vitro and in vivo models for determining the potency and/or biological activity of the polypeptides present in the atomized material will be clear to the skilled person and will depend on the intended disease and/or disorder to be prevented and/or treated. Suitable animal models for testing the potency and/or biological activity of SEQ ID NO's: 1 are e.g. described in WO 09/068627 and WO 09/147248. The potency and/or biological activity of SEQ ID NO: 2 to neutralize hRSV can for example be determined, in vitro, e.g. in a hRSV micro neutralization assay (see e.g. WO 09/147248) and, in vivo, e.g. in the cotton rat model for studies on RSV (Murphy et al., 1988, Virus Res. 11: 1-15).

Little to no loss of potency of the polypeptides of the invention has been observed upon atomization of compositions additionally comprising a surfactant at a concentration between 0.001% and 1% (v:v); upon atomization of compositions that contain the polypeptide of the invention at a concentration of 20 mg/mL or more, such as e.g. at a concentration of 25 mg/mL or more, or at a concentration of 50 mg/ml or even more; and/or when a vibrating-mesh nebulizer was used for atomization of the composition.

Accordingly, the present invention relates to a method for the preparation of an aerosol of immunoglobulin single variable domains wherein more than 80%, more than 85%, more than 90%, more than 95%, more than 98%, more than 99%, or more than 99.5% of the initial biological activity of the immunoglobulin variable domain is retained, said method comprising the step of atomizing a composition comprising an aqueous carrier and a polypeptide comprising one or more immunoglobulin single variable domains at a concentration of 1 mg/mL to 200 mg/mL, wherein:
  the composition further comprises a surfactant at a concentration between 0.001% and 1% (v:v);
  the polypeptide comprising one or more immunoglobulin single variable domains is present in the composition at a concentration of 20 mg/mL or more; and/or
  the composition is atomized in a vibrating-mesh nebulizer.

In one aspect, the present invention relates to a method for the preparation of an aerosol of immunoglobulin single variable domains wherein more than 80%, more than 85%, more than 90%, more than 95%, more than 98%, more than 99%, or more than 99.5% of the initial biological activity of the immunoglobulin variable domain is retained, said method comprising the step of atomizing a composition comprising an aqueous carrier and a polypeptide comprising one or more immunoglobulin single variable domains at a concentration of 1 mg/mL to 200 mg/mL, wherein the composition further comprises a surfactant at a concentration between 0.001% and 1% (v:v); and/or the composition is atomized in a vibrating-mesh nebulizer.

In another aspect, the present invention relates to a method for the preparation of an aerosol of immunoglobulin single variable domains wherein more than 80%, more than 85%, more than 90%, more than 95%, more than 98%, more than 99%, or more than 99.5% of the initial biological activity of the immunoglobulin variable domain is retained, said method comprising the step of atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition further comprises a surfactant at a concentration between 0.001% and 1% (v:v); and/or the composition is atomized in a vibrating-mesh nebulizer.

In yet another aspect, the present invention relates to a method for the preparation of an aerosol of immunoglobulin single variable domains wherein more than 80%, more than 85%, more than 90%, more than 95%, more than 98%, more than 99%, or more than 99.5% of the initial biological activity of the immunoglobulin variable domain is retained, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, and/or the composition is atomized in a vibrating-mesh nebulizer.

In still another aspect, the present invention relates to a method for the preparation of an aerosol of immunoglobulin single variable domains wherein more than 80%, more than 85%, more than 90%, more than 95%, more than 98%, more than 99%, or more than 99.5% of the initial biological activity of the immunoglobulin variable domain is retained, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the composition does not comprise a surfactant; and/or the composition is atomized in a vibrating-mesh nebulizer.

Accordingly, in the atomized material obtained in the method of the invention preferably:
- less than 7% (more preferably less than 6%, less than 5%, even more preferably less than 4%, less than 3%, less than 2%, or most preferably less than 1%) of the polypeptide of the invention forms aggregates (as defined herein);
- at least 80% (at least 85%, at least 90%, at least 95%, at least 98%, at least 99%, or at least 99.5%) of the polypeptide of the invention retains its binding activity (e.g. as assessed by ELISA and/or Biacore) to at least one (preferably to all) of its targets.

The polypeptide comprising or essentially consisting of one or more immunoglobulin single variable domains for use in the methods and compositions of the invention may be therapeutic or prophylactic, and may be useful in the treatment and/or management of one or more diseases. In one specific aspect, the polypeptide comprises or essentially consists of one immunoglobulin single variable domain. In another aspect, the polypeptide comprises or essentially consists of at least two immunoglobulin single variable domains. In another specific aspect, the polypeptide comprises or essentially consists of at least three immunoglobulin single variable domains.

The polypeptide comprising or essentially consisting of one or more immunoglobulin single variable domains for use in the methods and compositions of the invention may recognize any target and preferably a target that is associated with one or more diseases. In one aspect, the polypeptide of the invention recognizes a target that is associated with one or more respiratory diseases. In another aspect, the polypeptide specifically recognizes hRSV. In another aspect, the polypeptide specifically recognizes IL-23. In a preferred aspect, the immunoglobulin single variable domains used in the polypeptide of the invention are selected from WO 09/068627 (such as e.g. SEQ ID NO's 2578, 2584 and/or 2585 of WO 09/068627), WO 2010/139808 (such as e.g. SEQ ID NO's: 142 of U.S. 61/265,014) and WO 08/028977 (such as e.g. SEQ ID NO: 62 of WO 08/028977). Preferred polypeptides of the invention can also be selected from SEQ ID NO's: 1, 2 and 3.

The concentration of polypeptide of the invention present in the composition of the invention can be any concentration of the polypeptide that provides the desired effect to the subject. The concentration of the polypeptide should at least be such, that an effective amount of the polypeptide can be delivered to the subject through pulmonary administration. In a preferred aspect, the concentration of the polypeptide of the invention is from 1 to 200 mg/mL such as about 1 mg/mL, about 2 mg/mL, about 5 mg/mL, about 10 mg/mL, about 15 mg/mL, about 20 mg/mL, about 25 mg/mL, about 30 mg/mL, about 40 mg/mL, about 50 mg/mL, about 60 mg/mL, about 65 mg/mL, about 70 mg/mL, about 80 mg/mL, about 90 mg/mL or about 100 mg/mL or more. In certain embodiments, the concentration of polypeptide of the invention can be 110 mg/mL or more, 120 mg/mL or more, 130 mg/mL or more, 140 mg/mL or more, 150 mg/mL or more or even 200 mg/mL or more.

In a specific aspect, the concentration of polypeptide of the invention in the composition of the invention is 20 mg/mL or more, such as e.g. 25 mg/mL or more, or 50 mg/ml or even more. The present inventors have shown that compositions comprising the polypeptide of the invention in amounts of 20 mg/mL or higher, such as e.g. 25 mg/mL or more, or 50 mg/ml or even more, show significant reduced aggregate formation upon aerosolization compared to compositions with a polypeptide concentration that is lower than 20 mg/ml. Accordingly, in one aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains, wherein the polypeptide comprising one or more immunoglobulin single variable domains is present in the composition at a concentration of 20 mg/mL or more, such as e.g. at a concentration of 25 mg/mL or more, or at a concentration of 50 mg/ml or even more. The invention also relates to an aerosol comprising liquid droplets obtainable by atomizing a composition comprising an aqueous carrier and a polypeptide comprising one or more immunoglobulin single variable domains, wherein the amount of aggregate formation in the aerosol is 6% or lower, the % of aggregate formation as determined by SE-HPLC, and wherein the polypeptide comprising one or more single variable domains is present in the composition at a concentration of 20 mg/mL or more, such as e.g. at a concentration of 25 mg/mL or more, or at a concentration of 50 mg/ml or even more. In a particular aspect, the concentration of polypeptide of the invention in the composition of the invention is 30 mg/mL, 40 mg/mL, 50 mg/mL, 60 mg/ml or more, 70 mg/ml or more, 80 mg/ml or even more. The invention further relates to such a composition suitable for the preparation of an aerosol of immunoglobulin single variable domains, wherein the amount of aggregate formation is 6% or lower, the % of aggregate formation as determined by SE-HPLC, said composition comprising an aqueous carrier and a polypeptide comprising one or more immunoglobulin single variable domains, wherein the polypeptide comprising one or more single variable domains is present in the composition at a concentration of 20 mg/mL or more, such as e.g. at a concentration of 25 mg/mL or more, or at a concentration of 50 mg/ml or even more.

Apart from and/or in addition to the concentration of the polypeptide of the invention in the composition of the invention, the presence of a surfactant in the composition of the invention also had a positive effect on the aggregate formation in the atomized material. Upon atomization of a composition comprising a surfactant, aggregate formation was significantly reduced compared to the atomization of a composition that did not contain the surfactant.

Accordingly, in one aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein the composition also comprises a surfactant at a concentration between 0.001% and 1% (v:v). The invention also relates to an aerosol comprising liquid droplets obtainable by atomizing a composition comprising an aqueous carrier and a polypeptide comprising one or more immunoglobulin single variable domains at a concentration of 1 mg/mL to 200 mg/mL, wherein the amount of aggregate formation in the aerosol is 6% or lower, the % of aggregate formation as determined by SE-HPLC, and wherein the composition further comprises a surfactant at a concentration between 0.001% and 1% (v:v). The invention further relates to such a composition suitable for the preparation of an aerosol of immunoglobulin single variable domains wherein the amount of aggregate formation is 6% or lower, the % of aggregate formation as determined by SE-HPLC, said composition comprising an aqueous carrier and a polypeptide comprising one or more immunoglobulin single variable domains at a concentration of 1 mg/mL to 200 mg/mL, wherein the composition further comprises a surfactant at a concentration between 0.001% and 1% (v:v).

The positive effect of the presence of a surfactant in the composition of the invention on the aggregate formation in the atomized material was most significant upon atomization of compositions that contain the polypeptide of the invention at a concentration of lower than 20 mg/ml, such as e.g. at a concentration of 5 mg/ml, 10 mg/ml or 15 mg/ml.

Accordingly, in another aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition also comprises a surfactant at a concentration between 0.001% and 1% (v:v). The invention also relates to an aerosol comprising liquid droplets obtainable by atomizing a composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the amount of aggregate formation in the aerosol is 6% or lower, the % of aggregate formation as determined by SE-HPLC, and wherein the composition further comprises a surfactant at a concentration between 0.001% and 1% (v:v). The invention further relates to such a composition suitable for the preparation of an aerosol of immunoglobulin single variable domains wherein the amount of aggregate formation is 6% or lower, the % of aggregate formation as determined by SE-HPLC, said composition comprising an aqueous carrier and a polypeptide comprising one or more immunoglobulin single variable domains at a concentration of lower than 20 mg/ml, such as e.g. at a concentration of 5 mg/ml, 10 mg/ml or 15 mg/ml, wherein the composition further comprises a surfactant at a concentration between 0.001% and 1% (v:v).

The reduction of aggregate formation in the atomized material of compositions of the invention that contain the polypeptide of the invention at a concentration of 20 mg/mL or more, such as e.g. at a concentration of 25 mg/mL or more, or at a concentration of 50 mg/ml or even more, was less pronounced in the presence of a surfactant. In addition, the relative amount of high molecular weight aggregates was increased in the atomized material of these compositions in the presence of a surfactant.

Accordingly, in yet another aspect, the present invention relates to a method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the composition does not comprise a surfactant. The invention also relates to an aerosol comprising liquid droplets obtainable by atomizing a composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the amount of aggregate formation in the aerosol is 6% or lower, the % of aggregate formation as determined by SE-HPLC, and wherein the composition does not comprise a surfactant. The invention further relates to such a composition suitable for the preparation of an aerosol of immunoglobulin single variable domains wherein the amount of aggregate formation is 6% or lower, the % of aggregate formation as determined by SE-HPLC, said composition comprising an aqueous carrier and a polypeptide comprising one or more immunoglobulin single variable domains at a concentration of 20 mg/mL or more, such as e.g. at a concentration of 25 mg/mL or more, or at a concentration of 50 mg/ml or even more, wherein the composition does not comprise a surfactant.

A surfactant refers to a surface-active agent comprising a hydrophobic portion and a hydrophilic portion. In a preferred aspect, the surfactant is non-ionic. Certain exemplary non-ionic surfactants include (without being limiting) fatty alcohol, polysorbates, including without being limiting, polysorbate 80 (Tween 80) and polysorbate 20 (Tween 20), Triton X-100, polyoxypropylene-polyoxyethylene copolymer (Pluronic®), and nonyl phenoxypolyethoxylethanol (NP-40). Other surfactants which can be used in the composition of the invention include (without being limiting) phosphoglycerides, such as phosphatidyl cholines (lecithin), such as the naturally occurring surfactant, dipalmitoyl phosphatidyl choline (DPPC). Other exemplary surfactants include diphosphatidyl glycerol (DPPG), hexadecanol, polyoxyethylene-9-lauryl ether, a surface active fatty acid, such as palmitic acid or oleic acid, sorbitan trioleate (Span 85), glycocholate, surfactin, a poloxamer, a sorbitan fatty acid ester such as sorbitan trioleate, tyloxapol and a phospholipid. In a specific aspect, the surfactant is selected from Tween 20, Tween 80 or a poloxamer. Other compounds such as polyethyleneglycol (PEG) have surfactant like properties as they act on the air-water interface. In one aspect of the invention, the surfactant is not PEG. In particular, the composition does not comprise about 2% to about 10% PEG 1000 in 50 mM phosphate buffer containing 1.2% (w/v) sucrose). The concentration of the surfactant may range from between 0.001% and 1% (v:v) (preferably between 0.001% and 0.1% (v:v), or between 0.01% and 0.1% (v:v) such as about 0.001% (v:v), 0.005% (v:v), 0.01% (v:v), 0.02% (v:v), 0.05% (v:v), 0.08% (v:v), 0.1% (v:v), 0.5% (v:v), or 1% (v:v) of the composition, preferably from about 0.04% to 0.08% (v:v)). In a specific embodiment, the surfactant is Tween 20 or Tween 80, which is at a concentration of 0.001% (v:v), 0.005% (v:v), 0.01% (v:v), 0.02% (v:v), 0.04%, 0.05% (v:v), 0.08% (v:v), 0.1% (v:v), 0.5% (v:v) or 1% (v:v) of the composition, preferably 0.04% to 0.08% (v:v), in particular 0.04% (v:v).

An example of a preferred composition of the invention with these characteristics comprises 0.01% (v:v) Tween 80, 0.02% (v:v) Tween 80, 0.04% (v:v) Tween 80 or 0.08% (v:v) Tween 80.

The carrier comprised in the composition of the invention preferably is an aqueous carrier such as e.g. distilled water, MilliQ water or Water for Injection (WFI). The pH of the composition of the invention generally should not be equal to the isoelectric point of the particular polypeptide of the invention present in the composition and may range from about 5.5 to about 7.5, or from about 6.0 to about 7.5, preferably from about 6.5 to 7.5, most preferably from about 6.5 to 7.0, such as pH 6.0, pH 6.5 or pH7.0, in particular pH 7.0.

The composition can be buffered by any buffer that is pharmaceutical acceptable. Preferred buffers for use in the composition of the invention include (without being limiting) PBS, phosphate buffer, TrisHCl, histidine buffer and citrate buffer, such as e.g. histidine pH 6.0-6.5, phosphate buffer pH 7.0, TrisHCl pH 7.5 and citrate buffer/phosphate buffer pH 6.5, in particular phosphate ($NaH_2PO_4$/$Na_2HPO_4$) buffer pH 7.0.

The concentration of the buffer present in the composition of the invention may range from 1 mM to 100 mM, 5 mM to 100 mM, 5 mM to 75 mM, 5 mM to 50 mM, 10 mM to 50 mM. In a specific aspect, the concentration of buffer in the compositions of the invention is 1 mM, 2 mM, 5 mM, 10 mM, 15 mM, 20 mM, 25 mM, 50 mM, 75 mM, or 100 mM. Preferably, the concentration is between 10 and 50 mM, such as 10 mM or 50 mM, in particular 10 mM.

It will be understood by one skilled in the art that the composition of the invention may be isotonic or slightly hypotonic with human blood, i.e. the composition of the invention has essentially the same or a slightly lower osmotic pressure as human blood. Such isotonic or slightly hypotonic composition generally has an osmotic pressure from about 240 mOSm/kg to about 320 mOSm/kg, such as about 240 mOSm/kg or higher, 250 mOSm/kg or higher or 260 mOSm/kg or higher.

Tonicity of a composition can be adjusted by the use of tonicity modifiers. "Tonicity modifiers" are those pharmaceutically acceptable inert substances that can be added to the composition to provide an isotonicity of the composition. A preferred tonicity modifier in the composition of the invention are excipients. Preferred excipients for use in the composition of the invention may be selected from sugars, polyols, surfactants and salts. In one aspect, osmolality of the composition of the invention is adjusted by the addition of a sugar/polyol or an inorganic salt. Sugars/polyols may include (without being limiting) sucrose and lactose, as well as sugar derivatives including sugar alcohols and sugar acids. Polyols and sugar alcohols may include (without being limiting) mannitol, xylitol, erythritol, threitol, sorbitol and glycerol. Other exemplary sugars include (without being limiting) trehalose, glycine, maltose, raffinose, etc. The concentration of this excipient may range from about 1% to 10% (w:v), preferably from about 2.5% to 10% (w:v), more preferably from about 5% to 10% (w:v), such as e.g. 5% (w:v), 7.5% (w:v), 8% or 10% (w:v). Without being limiting, inorganic salts for adjusting the osmolality of the composition of the invention include NaCl, KCl, $CaCl_2$, and $MgCl_2$, in particular NaCl. The concentration of inorganic salt may range from 10 mM to 200 mM, 10 mM to 150 mM, 50 mM to 150 mM, 100 mM to 150 mM, or 100 mM to 120 mM. In a specific aspect, the concentration of salt (preferably NaCl) which may be included in the formulations of the invention may be about 10 mM, about 25 mM, about 50 mM, about 75 mM, about 100 mM, about 110 mM, about 120 mM, about 130 mM, about 150 mM, or about 200 mM.

An example of a preferred composition of the invention with these characteristics comprises 10 mM phosphate ($NaH_2PO_4$/$Na_2HPO_4$) buffer pH 7.0 and 130 mM NaCl. Accordingly, in one aspect, the composition of the invention comprises 10 mM phosphate ($NaH_2PO_4$/$Na_2HPO_4$) buffer pH 7.0, 130 mM NaCl and a polypeptide comprising one or more immunoglobulin single variable domains as described above. In a particular aspect, the composition of the invention comprises 10 mM phosphate ($NaH_2PO_4$/$Na_2HPO_4$) buffer pH 7.0, 130 mM NaCl and the polypeptide with SEQ ID NO: 2. In another aspect, the composition of the invention comprises 10 mM phosphate ($NaH_2PO_4$/$Na_2HPO_4$) buffer pH 7.0, 130 mM NaCl and the polypeptide with SEQ ID NO: 2 at a concentration of 20 mg/mL or more, such as e.g. at a concentration of 25 mg/mL or more, or at a concentration of 50 mg/ml or even more, preferably at a concentration of 50 mg/ml.

Other pharmaceutically acceptable carriers may also be used in a formulation of the present application. The phrase "pharmaceutically acceptable carrier" as used herein means a pharmaceutically acceptable material, composition or vehicle, such as a liquid or solid filler, diluent, excipient, solvent or encapsulating material, involved in carrying or transporting the agent (e.g. prophylactic or therapeutic agent). Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other non-toxic compatible substances employed in pharmaceutical formulations.

The compositions of the present invention are characterized by providing a high thermal stability to the polypeptides of the invention. Thermal stability can be evaluated e.g. by determining the melt temperature e.g. Tm. Suitable techniques for determining the melt temperature are known and include e.g. a thermal shift assay (TSA) e.g. as described herein. More specifically, the compositions of the present invention lead to an increase of Tm for the polypeptides of the invention as determined by TSA in comparison to other formulations. This effect is exemplified in Table 3 of the experimental section.

According to the present invention, the compositions of the invention have a positive influence on Tm over a broad range of pH values, e.g. between 5.5 and 6.5 for citrate buffer, and 7.0 to 7.5 for phosphate buffer. The most advantageous effect on Tm can be observed for phosphate buffer at pH 7.0 to 7.5, in particular 7.0±0.2.

As evidenced by the experimental section of this description, Tm as determined by TSA serves as a valuable indicator for stability of the polypeptides of the invention. Increasing Tm indicate increased stability also in other physicochemical parameters, and can therefore indicate particularly preferable embodiments of the invention.

General methods for producing the immunoglobulin single variable domains and/or polypeptides present in the composition of the invention are known to the skilled person and/or have been described in the art. The immunoglobulin single variable domains and/or polypeptides can be produced in any host known to the skilled person. For example but without being limiting, the immunoglobulin single variable domains and/or polypeptides can be produced in prokaryotic hosts among which *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*. Production of immunoglobulin single variable domains in prokaryotes and lower eukaryotic hosts such as *Pichia pastoris* has been described e.g. in WO 94/04678, WO 94/25591 and WO 08/142164. The contents of these applications are explicitly referred to in the connection with general culturing techniques and methods, including suitable media and conditions. The contents of these documents are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the method for the expression and/or production of a polypeptide comprising one or more immunoglobulin single variable domains at least comprises the steps of:
a) cultivating a host or host cell under conditions that are such that said host or host cell will multiply;
b) maintaining said host or host cell under conditions that are such that said host or host cell expresses and/or produces the polypeptide;
c) isolating and/or purifying the secreted polypeptide from the medium.

To produce/obtain expression of the polypeptide, the transformed host cell or transformed host organism may generally be kept, maintained and/or cultured under conditions such that the (desired) polypeptide is expressed/produced. Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

The polypeptide of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic interaction chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (obtained by centrifugation) is captured on any combination of columns selected from (without being limiting) affinity chromatography resin such as Protein A resin, Cation Exchange Chromatography (CIEC) or an Anion Exchange Chromatography (AIEC) using for example Poros 50HS (POROS), SOURCE 30S or SOURCE 15S (GE Healthcare), SP Sepharose (GE Healthcare), Capto S (GE Healthcare), Capto MMC (GE Healthcare) or Poros 50HQ (POROS), SOURCE 30Q or SOURCE 15Q (GE Healthcare), Q Sepharose (GE Healthcare), Capto Q and DEAE Sepharose (GE Healthcare), Size exclusion chromatography (SE-HPLC) using for example Superdex 75 or Superdex 200 (GE Healthcare), hydrophobic interaction chromatography (HIC) using for example octyl, butyl sepharose or equivalents, optionally also including a tangential flow filtration (TFF) step. Any combination of columns can be used for the purification of the polypeptides of the invention, such as e.g. Protein A resin followed by Cation Exchange Chromatography or two Cation Exchange Chromatography steps.

The present invention also provides methods for preparing the compositions of the invention comprising the polypeptides of the invention. More particularly, the present invention provides methods for preparing compositions of such polypeptides, said methods comprising concentrating a fraction containing the purified polypeptide to the final polypeptide concentration using e.g. a semipermeable membrane with an appropriate molecular weight (MW) cutoff (e.g. a 5 kD cutoff for single variable domains; a 10 kD cutoff for bivalent polypeptides comprising two single variable domains; or a 15 kD cutoff for trivalent polypeptides comprising three single variable domains) and diafiltering and/or ultrafiltering to buffer exchange and further concentrate the polypeptide fraction into the selected buffer using the same membrane.

Surfactant (e.g. Tween 20, Tween 80 or poloxamer) can be added after the final diafiltration/ultrafiltration step at a concentration in the range between 0% and 1%, preferably between 0.001% and 0.1%, or between 0.01% and 0.1% such as about 0.001%, 0.005%, 0.01%, 0.02%, 0.04%, 0.05%, 0.08%, 0.1%, 0.5%, or 1% of the composition, preferably 0.04% to 0.08%, in particular 0.04%.

The composition of the present invention may be sterilized by various sterilization methods, including sterile filtration, radiation, etc. In a specific embodiment, the polypeptide composition is filter-sterilized with a presterilized 0.2 micron filter.

Preferably, the composition of the present invention is supplied in a hermetically sealed container. Liquid compositions may comprise a quantity between 1 mL and 20 mL, preferably about 1 mL, 2 mL, 3 mL, 4 mL, 5 mL, 6 mL, 7 mL, 8 mL, 9 mL, 10 mL, 15 mL, or 20 mL.

The composition of the present invention can be prepared as unit dosage forms by preparing a vial containing an aliquot of the composition for a one time use. For example, a unit dosage of liquid composition per vial may contain 1 mL, 2 mL, 3 mL, 4 mL, 5 mL, 6 mL, 7 mL, 8 mL, 9 mL, 10 mL, 15 mL, or 20 mL of the composition. The pharmaceutical unit dosage forms should be suitable for pulmonary delivery of the polypeptide by aerosol.

The amount of a composition of the present invention which will be effective in the prevention, treatment and/or management of a certain disease or disorder can be determined by standard clinical techniques well-known in the art or described herein. Effective doses may be extrapolated from dose-response curves derived from in vitro or animal model test systems. For compositions of the polypeptide, encompassed by the invention, the dosage administered to a patient may further be calculated using the patient's weight in kilograms (kg) multiplied by the dose to be administered in mg/kg. Also useful for dose calculations may be the percentage of the applied dose that reaches the lung and/or the percentage of the applied dose that reaches the systemic circulation (depending on the disease to be prevented and/or treated and the location in the body of the prophylactic and/or therapeutic activity of the agent).

The required volume (in mL) to be given is then determined by taking the mg dose required divided by the concentration of the polypeptide composition. The final calculated required volume will be obtained by pooling the contents of as many vials as are necessary.

The present invention also encompasses a finished packaged and labelled pharmaceutical product. This article of manufacture or kit includes the appropriate unit dosage form in an appropriate vessel or container such as a glass vial or other container that is hermetically sealed. The unit dosage form should be suitable for pulmonary delivery by aerosol. Preferably, the article of manufacture or kit further comprises instructions how to use the composition in an aerosol delivery system. The instructions may further contain informational material that advise the physician, technician or patient on how to appropriately prevent or treat the disease or disorder in question. In other words, the article of manufacture includes instruction means indicating or suggesting a dosing regimen for use in the aerosol delivery system including, but not limited to, actual doses, monitoring procedures, and other monitoring information.

As with any pharmaceutical product, the packaging material and container are designed to protect the stability of the product during storage and shipment.

The compositions, containers, pharmaceutical unit dosages and kits of the present invention should be suitable for delivery of the polypeptide of the invention by pulmonary administration, i.e. aerosolization. Accordingly, the compositions, containers, pharmaceutical unit dosages and kits of the present invention should be suitable for use in an aerosol delivery system (as further defined herein). Accordingly, the present invention also relates to the use of a composition of the invention for the preparation of a medicament for delivery to a human subject by aerosolization. In one aspect, the composition of the invention is used for the preparation of a medicament for delivery to a human subject by nebulisation, preferably in a vibrating-mesh nebulizer.

The present invention also provides for aerosol delivery systems that can be used in the method of the invention (for the preparation of an aerosol) and/or for the delivery of the compositions of the invention by aerosolization. The aerosol delivery system of the invention may comprise a container comprising the composition of the invention and an aerosol generator connected to it. The aerosol generator is constructed and arranged to generate an aerosol of the composition of the invention. Without being limiting, aerosol generators include nebulizers, mechanical pumps and pressurized containers.

In one aspect, the aerosol delivery system may include a pressurized container containing the composition of the invention. The pressurized container typically has an actuator connected to a metering valve so that activation of the actuator causes a predetermined amount of the composition within the container to be dispensed from the container in the form of an aerosol. Pressurized containers of this type are well known in the art as propellant-driven metered-dose inhalers (pMDIs or simply MDIs). MD's typically include an actuator, a metering valve, and a pressurized container that holds a micronized drug suspension or solution, liquefied propellant, and surfactant (e.g., oleic acid, sorbitan trioleate, lecithin). Pressurized metered dose inhalers (pMDIs) are the most commonly used inhaler worldwide. The aerosol is created when a valve is opened (usually by pressing down on the propellant canister), allowing liquid propellant to spray out of a canister. Typically, a drug or therapeutic is contained in small particles (usually a few microns in diameter) suspended in the liquid propellant, but in some formulations the drug or therapeutic may be dissolved in the propellant. The propellant evaporates rapidly as the aerosol leaves the device, resulting in small drug or therapeutic particles that are inhaled. Propellants used in such pMDIs include but are not limited to hydrofluoroalkanes (HFAs). Historically these MD's typically used chlorofluorocarbons (CFCs) as propellants, including trichlorofluoromethane, dichlorodifluoromethane, and dichlorotetrafluoro-methane. Newer propellants may include 1,1,1,2-tetrafluoroethane and 1,1,1,2,3,3,3-heptafluoropropane. Other solvents or excipients may also be employed with pMDIs, such as ethanol, ascorbic acid, sodium metabisulfate, glycerin, chlorobutanol, and cetylpyridium chloride. Such pMDIs may further include add-on devices such as, for example, spacers, holding chambers and other modifications.

The Sonik LDI Aerosolization Technology (Drug Delivery Technology, Montville, N.J., US) is used primarily for delivery of liquid medications and occasionally powders. The proprietary nozzle is powered by compressed gas, normally carbon dioxide ($CO_2$), to deliver consistent bursts of medication with each actuation of the device. After the compressed gas exits from the primary jet of the Sonik LDI nozzle, a chain of reflected compression and refraction shock waves is formed. The nozzle introduces liquid medication into the chain of shock waves within a shock chamber to produce a consistent and high-quality burst of aerosol. Upon exit from the Sonik LDI nozzle, the aerosol/gas stream is forced down through an amplification chamber, where secondary aerosolization processes cause an increase in respirable particles and a decrease in residual spray. $CO_2$ is used as the driving propellant, principally because it is inexpensive and may be easily stored in compact disposable canisters. Unlike MDIs, the Sonik LDI Aerosolization Technology does not mix propellant and medication until the moment of aerosolization. This delayed approach allows liquid (or powder) medication to be stored in sealed blisters and eases the development burden of formulation stability. This technology is adaptable to a number of configurations: breath-actuated aerosol holding chambers, compact low-velocity direct oral entry, pre-packaged unit-dose medications, and patient- or clinician-filled reservoir devices.

In another aspect of the invention, the aerosol delivery system may be a nebulizer. Nebulizers produce a mist of drug-containing liquid droplets for inhalation. "Nebulization", as used in the present invention, means the conversion of a liquid to a fine spray. Nebulizers mix medicine with compressed air to create a fine mist that the patient breathes in through a facemask or mouthpiece. For children, nebulization is one of the easiest and most effective ways to administer medicine to the lungs. Using appropriately sized masks that fit infants, or mouthpieces for older children and adults, patients simply breathe normally until all the medicine has been inhaled. Another advantage of nebulization, particularly for young children, is that it requires no special technique to get the medicine into the lungs.

Nebulizers are usually classified into two types: ultrasonic nebulizers and jet nebulizers. Airjet nebulizers for atomization are considered portable because of the availability of small compressed air pumps, but they are relatively large and inconvenient systems. Ultrasonic nebulizers have the advantage of being more portable because they generally do not require a source of compressed air.

Air-jet nebulizers convert liquid into aerosols by means of a high velocity gas passing through a narrow "venturi" nozzle. The fluid in the nebulizer reservoir is drawn up a feed tube and emerges as fine filaments that collapse into aerosol droplets due to surface tension. Baffles within the nebulizer remove larger droplets. The droplet size in the airstream is influenced by the compressed air pressure. Mass median diameters normally range from 2 to 5 μm with air pressures of 20 to 30 psig. Examples of jet nebulizers include (without being limiting) Pari LC Jet Plus (PARI Gmbh, Grafelingen, Germany), Hudson T Up-draft II (Hudson RCI, Kernen, Germany), Raindrop (Puritan Bennett, Boulder, Colo., US).

Ultrasonic nebulizers generate aerosols using high-frequency ultrasonic waves (i.e., 100 kHz and higher) focused in the liquid chamber by a ceramic piezoelectric crystal that mechanically vibrates upon stimulation (Dennis et al., 1992, J. Med. Eng; Tech. 16: 63-68; O'Doherty et al., 1992, Am. Rev. Respir. Dis. 146: 383-88). A fountain of fluid is produced at the air-fluid interface. Small droplets are generated from the lower regions of the fountain whilst large droplets are generated from the apex. In some instances, an impeller blows the particles out of the nebulizer or the aerosol is inhaled directly by the patient. The ultrasonic nebulizer is capable of greater output than the airjet nebulizer and for this reason is used frequently in aerosol drug therapy. Examples of ultrasonic nebulizers include (without being limiting) Mabis Mist II (Allergy Asthma Techology LLC), DeVilbiss Compressor Nebulizer Systems, DeVilbiss Reusable Jet Nebulizers (DeVilbiss Healthcare, Somerset, Pa., US), Kun-88 (K-Sonic, Taipei, Taiwan), SUN 345 (Siemens, Elema AB, Solna, Sweden).

In both air-jet and ultrasonic nebulizers baffles in the nebulizer trap and recycle the large (primary) aerosol droplets, whilst small (secondary) droplets are released for inhalation. In either type of nebulizer, the drug is usually contained in solution in the liquid in the nebulizer and so the droplets being produced contain drug in solution.

Ultrasonic nebulizers are generally unsuitable for delivery of suspensions (Taylor and McCallion, 2002, In: Swarbrick, Boylan (Eds.), Encyclopedia of Pharmaceutical Technology, 2nd ed. Marcel Dekker, Inc., New York, pp. 2840-2847) and liposomes (Elhissi and Taylor, 2005, J. Drug Deliv. Sci. Technol. 15: 261-265), and due to heat generation during atomization they may degrade labile substances such as proteins (Niven et., 1995, Pharm. Res. 12: 53-59).

Vibrating-mesh nebulizers may overcome the drawbacks of air-jet and ultrasonic nebulizers. Vibrating-mesh devices employ perforated plates which vibrate in order to generate the aerosol. Activation of the vibrational element to vibrate the aperture plate causes the composition of the invention to be drawn through the plurality of apertures to create a low-velocity aerosol with a defined range of droplet (i.e. particle) sizes. These nebulizers do not heat the fluid during atomization and have been shown to be suitable for delivery of suspensions (Fink, and Simmons, 2004. Chest 126: 816S), and delicate structures such as liposomes (Wagner, 2006, J. Liposome Res. 16: 113-125) and nucleic acids (Lentz, 2006, J. Aerosol Med. 19: 372-384). Vibrating-mesh nebulizers are divided into passively and actively vibrating-mesh devices (Newman, 2005, J. Appl. Ther. Res. 5: 29-33). Passively vibrating-mesh devices (e.g. Omron MicroAir NE-U22 nebulizer) employ a perforated plate having up to 6000 micron sized holes. A vibrating piezo-electric crystal attached to a transducer horn induces "passive" vibrations in the perforated plate positioned in front of it, resulting in extrusion of fluid through the holes and generation of the aerosol. Actively vibrating-mesh devices (e.g. Aeroneb Pro nebulizer) may employ a "micropump" system which comprises an aerosol generator consisting of a plate with up to 1000 dome-shaped apertures and a vibrating element which contracts and expands on application of an electric current. This results in upward and downward movements of the mesh by a few micrometers, extruding the fluid and generating the aerosol. Other examples of vibrating-mesh nebulizers include eFlow® (PARI GmbH, Grafelingen, Germany; see also U.S. Pat. No. 5,586,550), Aeroneb® (Aerogen, Inc., Sunnyvale, Calif.; see also U.S. Pat. Nos. 5,586,550; 5,938,117; 6,014,970; 6,085,740; 6,205,999).

Accordingly, in one aspect, the present invention relates to a method for the preparation of an aerosol of immunoglobulin single variable domains, wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 1 mg/ml to 200 mg/ml, wherein the composition is atomized in a vibrating mesh nebulizer. The invention also relates to an aerosol comprising liquid droplets obtainable by atomizing a composition comprising an aqueous carrier and a polypeptide comprising one or more immunoglobulin single variable domains at a concentration of 1 mg/ml to 200 mg/ml, wherein the amount of aggregate formation in the aerosol is 6% or lower, the % of aggregate formation as determined by SE-HPLC, and wherein the composition is atomized in a vibrating mesh nebulizer. The invention further relates to a vibrating mesh nebulizer comprising a container and an aerosol generator connected to the container, wherein the container comprises a composition of the invention.

The compositions, containers, aerosol delivery systems, pharmaceutical unit dosages and/or kits of the present invention may be administered to a subject to prevent, treat and/or manage one or more specific disease and/or disorder. In a specific aspect, the compositions, containers, aerosol delivery systems, pharmaceutical unit dosages and/or kits of the present invention are administered to a subject to prevent, treat and/or manage one or more respiratory disease and/or disorder.

Respiratory diseases and/or disorders that can be treated, suppressed or prevented using the compositions, containers, aerosol delivery systems, pharmaceutical unit dosages and/or kits of the invention may include lung inflammation, chronic obstructive pulmonary disease, asthma, pneumonia, hypersensitivity pneumonitis, pulmonary infiltrate with eosinophilia, environmental lung disease, pneumonia, bronchiectasis, cystic fibrosis, interstitial lung disease, primary pulmonary hypertension, pulmonary thromboembolism, disorders of the pleura, disorders of the mediastinum, disorders of the diaphragm, hypoventilation, hyperventilation, sleep apnea, acute respiratory distress syndrome, mesothelioma, sarcoma, graft rejection, graft versus host disease, lung cancer, allergic rhinitis, allergy, asbestosis, aspergilloma, aspergillosis, bronchiectasis, chronic bronchitis, emphysema, eosinophilic pneumonia, idiopathic pulmonary fibrosis, invasive pneumococcal disease, influenza, nontuberculous mycobacteria, pleural effusion, pneumoconiosis, pneumocytosis, pneumonia, pulmonary actinomycosis, pulmonary alveolar proteinosis, pulmonary anthrax, pulmonary edema, pulmonary embolus, pulmonary inflammation, pulmonary histiocytosis X, pulmonary hypertension, pulmonary nocardiosis, pulmonary tuberculosis, pulmonary veno-occlusive disease, rheumatoid lung disease, sarcoidosis, Wegener's granulomatosis, and non-small cell lung carcinoma. In a specific aspect, the compositions, containers, aerosol delivery systems, pharmaceutical unit dosages and/or kits of the present invention are administered to a subject to prevent, treat and/or manage viral lung infections and more particularly hRSV infections.

In another aspect, the compositions, containers, aerosol delivery systems, pharmaceutical unit dosages and/or kits of the invention are used for systemic delivery of a polypeptide of the invention by pulmonary administration by aerosolization. Accordingly, the compositions, containers, aerosol delivery systems, pharmaceutical unit dosages and/or kits of the present invention may be administered to a subject to prevent, treat and/or manage any disease and/or disorder associated with the target to which the polypeptide of the invention (present in the composition, container, aerosol delivery system, pharmaceutical unit dosage and/or kit) specifically binds. For example, without being limiting, the composition, container, aerosol delivery system, pharmaceutical unit dosage and/or kit can be used to prevent, treat and/or manage diseases and/or disorders associated with heterodimeric cytokines and their receptors including inflammation and inflammatory disorders such as bowel diseases (colitis, Crohn's disease, IBD), infectious diseases, psoriasis, cancer, autoimmune diseases (such as MS), carcoidis, transplant rejection, cystic fibrosis, asthma, chronic obstructive pulmonary disease, rheumatoid arthritis, viral infection, common variable immunodeficiency.

Also encompassed within the scope of the present invention is the prevention and/or treatment with the compositions, containers, aerosol delivery systems, pharmaceutical unit dosages and/or kits of the invention of one or more diseases and/or disorders as described above.

The compositions, containers, aerosol delivery systems, pharmaceutical unit dosages and/or kits of the present invention may also be advantageously utilized in combination with one or more other therapies (e.g., one or more other prophylactic or therapeutic agents), preferably therapies useful in the prevention, treatment and/or management of the (same or another) disease and/or disorder. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, other immunoglobulin single variable domains, synthetic or natural inorganic molecules, mimetic agents, and synthetic or natural organic molecules. Any therapy (e.g., prophylactic or therapeutic agents) which is known to be useful, or which has been used or is currently being used for the prevention, treatment and/or management of one or more symptoms associated with a specific disease or disorder, can be used in combination with the compositions of the present invention in accordance with the invention described herein.

A composition of the invention may be administered to a mammal, preferably a human, concurrently with one or more other therapies (e.g., one or more other prophylactic or therapeutic agents). The term "concurrently" is not limited to the administration of prophylactic or therapeutic agents/therapies at exactly the same time, but rather it is meant that the composition of the invention and the other agent/therapy are administered to a mammal in a sequence and within a time interval such that the polypeptide contained in the composition can act together with the other agent/therapy to provide an increased benefit than if they were administered otherwise. For example, the composition of the invention and the one or more other prophylactic or therapeutic agents may be administered at the same time or sequentially in any order at different points in time; however, if not administered at the same time, they should be administered sufficiently close in time so as to provide the desired therapeutic or prophylactic effect.

When used in combination with other therapies (e.g., prophylactic and/or therapeutic agents), the compositions of the invention and the other therapy can act additively or synergistically. The invention contemplates administration of a composition of the invention in combination with other therapies (e.g., prophylactic or therapeutic agents) by the same or different routes of administration, e.g., pulmonary and parenteral.

The invention will now be further described by means of the following non-limiting preferred aspects and examples:

ASPECTS

1. Method for the preparation of an aerosol of immunoglobulin single variable domains wherein the amount of aggregate formation is 6% or lower, the % of aggregate formation as determined by SE-HPLC, said method comprising the step of atomizing a composition comprising an aqueous carrier and a polypeptide comprising one or more immunoglobulin single variable domains at a concentration of 1 mg/mL to 200 mg/mL, wherein:
   the composition further comprises a surfactant at a concentration between 0.001% and 1%;
   the polypeptide comprising one or more immunoglobulin single variable domains is present in the composition at a concentration of 20 mg/mL or more; and/or
   the composition is atomized in a vibrating-mesh nebulizer.
2. Method of aspect 1, wherein the amount of aggregate formation is 5% or lower, preferably 4% or lower, such as 3% or lower, 2% or lower or even 1% or lower.
3. Method of any of aspects 1 or 2, wherein the composition further comprises a surfactant at a concentration between 0.001% and 1%, preferably between 0.001% to about 0.1%, or about 0.01% to about 0.1% such as about 0.001%, 0.005%, 0.01%, 0.02%, 0.05%, 0.08% or 0.1%, preferably about 0.01%.
4. Method of any of aspects 1 to 3, wherein the surfactant is selected from a non-ionic detergent.
5. Method of any of aspects 1 to 4, wherein the surfactant is selected from polysorbates (such as e.g. Tween 20, and Tween 80) and poloxamers, or wherein PEG is added as a surfactant-like compound.
6. Method of any of aspects 3 to 5, wherein the polypeptide comprising one or more immunoglobulin single variable domains is present at a concentration of lower than 20 mg/mL.
7. Method of any of aspects 1 to 5, wherein the polypeptide comprising one or more immunoglobulin single variable domains is present at a concentration of 20 mg/mL or more.
8. Method of any of aspects 1 or 2, wherein the polypeptide comprising one or more immunoglobulin single variable domains is present at a concentration of 20 mg/mL or more and wherein the composition does not comprise a surfactant.
9. Method of any of aspects 1 to 8, wherein the polypeptide comprises one immunoglobulin single variable domain.
10. Method of any of aspects 1 to 8, wherein the polypeptide comprises two or more immunoglobulin single variable domains, such as two or three.
11. Method of any of aspects 1 to 10, wherein the polypeptide specifically binds RSV or IL-23.
12. Method of aspect 11, wherein the polypeptide is selected from one of SEQ ID NO's: 1, 2 and 3.
13. Method of any of aspects 1 to 12, wherein the composition is atomized in a nebulizer.
14. Method of aspect 13, wherein the nebulizer is a vibrating-mesh nebulizer.
15. Method of any of aspects 1 to 14, wherein the aerosol has a volume median diameter between 1 and 10 μm, preferably between 1 and 7 μm, most preferably between 1 and 5 μm, such as around 3, 3.5 or 4 μm.
16. Aerosol comprising liquid droplets obtainable by atomizing a composition comprising an aqueous carrier and a polypeptide comprising one or more immunoglobulin single variable domains at a concentration of 1 mg/mL to 200 mg/mL, wherein the amount of aggregate formation in the aerosol is 6% or lower, the % of aggregate formation as determined by SE-HPLC, and wherein:
   the composition further comprises a surfactant at a concentration between 0.001% and 1%;
   the polypeptide comprising one or more immunoglobulin single variable domains is present in the composition at a concentration of 20 mg/mL or more; and/or
   the composition is atomized in a vibrating-mesh nebulizer.
17. Aerosol of aspect 16, wherein the amount of aggregate formation in the aerosol is 5% or lower, preferably 4% or lower, such as 3% or lower, 2% or lower or even 1% or lower.
18. Aerosol of any of aspects 16 or 17, wherein the composition further comprises a surfactant at a concentration between 0.001% and 1%, preferably between 0.001% to about 0.1%, or about 0.01% to about 0.1% such as about 0.001%, 0.005%, 0.01%, 0.02%, 0.05%, 0.08% or 0.1%, preferably about 0.01%.
19. Aerosol of any of aspects 16 to 18, wherein the surfactant is selected from a non-ionic detergent.
20. Aerosol of any of aspects 16 to 19, wherein the surfactant is selected from polysorbates (such as e.g. Tween 20, and Tween 80) and poloxamers, or wherein PEG is added as a surfactant-like compound.
21. Aerosol of any of aspects 18 to 20, wherein the polypeptide comprising one or more immunoglobulin single variable domains is present at a concentration of lower than 20 mg/mL.
22. Aerosol of any of aspects 16 to 20, wherein the polypeptide comprising one or more immunoglobulin single variable domains is present at a concentration of 20 mg/mL or more.
23. Aerosol of any of aspects 16 or 17, wherein the polypeptide comprising one or more immunoglobulin single variable domains is present at a concentration of 20 mg/mL or more and wherein the composition does not comprise a surfactant.
24. Aerosol of any of aspects 16 to 23, wherein the polypeptide comprises one immunoglobulin single variable domain.
25. Aerosol of any of aspects 16 to 23, wherein the polypeptide comprises two or more immunoglobulin single variable domains, such as two or three.

26. Aerosol of any of aspects 16 to 25, wherein the polypeptide specifically binds RSV or IL-23.
27. Aerosol of aspect 26, wherein the polypeptide is selected from one of SEQ ID NO's: 1, 2 and 3.
28. Aerosol of any of aspects 16 to 27, wherein the composition is atomized in a nebulizer.
29. Aerosol of aspect 28, wherein the nebulizer is a vibrating-mesh nebulizer.
30. Aerosol of any of aspects 16 to 29, wherein the aerosol has a volume median diameter between 1 and 10 µm, preferably between 1 and 7 µm, most preferably between 1 and 5 µm, such as around 3, 3.5 or 4 μm.
31. A composition suitable for the preparation of an aerosol of immunoglobulin single variable domains wherein the amount of aggregate formation is 6% or lower, the % of aggregate formation as determined by SE-HPLC, said composition comprising an aqueous carrier and a polypeptide comprising one or more immunoglobulin single variable domains at a concentration of 1 mg/mL to 200 mg/mL, wherein:
   the composition further comprises a surfactant at a concentration between 0.001% and 1%; and/or
   the polypeptide comprising one or more immunoglobulin single variable domains is present in the composition at a concentration of 20 mg/mL or more.
32. The composition of aspect 31, wherein the amount of aggregate formation is 5% or lower, preferably 4% or lower, such as 3% or lower, 2% or lower or even 1% or lower.
33. The composition of any of aspects 31 or 32, which comprises a surfactant at a concentration between 0.001% and 1%, preferably between 0.001% to about 0.1%, or about 0.01% to about 0.1% such as about 0.001%, 0.005%, 0.01%, 0.02%, 0.05%, 0.08% or 0.1%, preferably about 0.01%.
34. The composition of any of aspects 31 to 33, wherein the surfactant is selected from a non-ionic detergent.
35. The composition of aspect 34, wherein the surfactant is selected from polysorbates (such as e.g. Tween 20, and Tween 80) and poloxamers, or wherein PEG is added as a surfactant-like compound.
36. The composition of any of aspects 33 to 35, wherein the polypeptide comprising one or more immunoglobulin single variable domains is present at a concentration of lower than 20 mg/mL.
37. The composition of any of aspects 31 to 35, wherein the polypeptide comprising one or more immunoglobulin single variable domain is present at a concentration of 25 mg/ml or more.
38. The composition of any of aspects 31 or 32, wherein the polypeptide comprising one or more immunoglobulin single variable domains is present at a concentration of 20 mg/mL or more and wherein the composition does not comprise a surfactant.
39. The composition of any of aspects 31 to 38, wherein the polypeptide comprises one immunoglobulin single variable domain.
40. The composition of any of aspects 31 to 38, wherein the polypeptide comprises two or more immunoglobulin single variable domains, such as two or three.
41. The composition of any of aspects 31 to 40, wherein the polypeptide specifically binds RSV or IL-23.
42. The composition of aspect 41, wherein the polypeptide is selected from one of SEQ ID NO's: 1, 2 and 3.
43. The method of any of aspects 1 to 15, the aerosol of any of aspects 16 to 30, or the composition of any of aspects 31 to 42, wherein the aqueous carrier in the composition is distilled water, MilliQ grade water or Water for Injection (WFI).
44. The method of any of aspects 1 to 15, the aerosol of any of aspects 16 to 30, or the composition of any of aspects 31 to 42, wherein the composition is buffered to pH 5.5 to 7.5, preferably pH 7.0.
45. The method, the aerosol, or the composition of aspect 44, wherein the composition is buffered with a buffer selected from PBS, phosphate buffer, TrisHCl, histidine buffer and citrate buffer, preferably phosphate buffer.
46. The method, the aerosol, or the composition of aspect 45, wherein the buffer in the composition has a concentration of 10 to 100 mM, preferably 10 to 50 mM, such as 10 mM or 20 mM, in particular 10 mM.
47. The method of any of aspects 1 to 15, the aerosol of any of aspects 17 to 30, or the composition of any of aspects 31 to 42, wherein the composition is isotonic or slightly hypotonic.
48. The method, the aerosol, or the composition of aspect 47, wherein the composition has an osmolality of 290±60 mOsm/kg.
49. The method, the aerosol, or the composition of any of aspects 47 or 48, wherein the osmolality in the composition has been adjusted by addition of a sugar or a salt, preferably NaCl, in particular 130 mM NaCl.
50. A method for the preparation of a composition of any of aspects 31 to 42, at least comprising the step of concentrating the polypeptide and exchanging it with the selected buffer.
51. The method of aspect 50, additionally comprising the step of adding a surfactant at a concentration between 0.001% and 1%, preferably between 0.001% to about 0.1%, or about 0.01% to about 0.1% such as about 0.001%, 0.005%, 0.01%, 0.02%, 0.05%, 0.08% or 0.1%, preferably about 0.01%.
52. The method of any of aspects 50 or 52, wherein the surfactant is selected from a non-ionic detergent.
53. The method of aspect 52, wherein the surfactant is selected from polysorbates (such as e.g. Tween 20, and Tween 80) and poloxamers, or wherein PEG is added as a surfactant-like compound.
54. The method of any of aspects 51 to 53, wherein the polypeptide is concentrated to a concentration of lower than 20 mg/m L.
55. The method of any of aspects 50 to 53, wherein the polypeptide is concentrated to a concentration of 20 mg/ml or more.
56. The method of aspect 50, wherein the polypeptide is concentrated to a concentration of 20 mg/mL or more and wherein no surfactant is added.
57. Use of a composition of any of aspects 31 to 42 for the preparation of a medicament for delivery to a human subject by aerosolization.
58. Use of a composition according to aspect 57, for the preparation of a medicament for delivery to a human subject by nebulization.
59. Use of a composition according to aspect 58, for the preparation of a medicament for delivery to a human subject by nebulisation in a vibrating-mesh nebulizer.
60. A container containing a composition according to any of aspects 31 to 42.
61. A kit comprising one or more of the containers according to aspect 60, and instructions for use of the composition for administration in an aerosol delivery system.
62. The kit of aspect 61, wherein the aerosol delivery system is a nebulizer.

63. The kit of aspect 62, wherein the nebulizer is a vibrating-mesh nebulizer.
64. An aerosol delivery system comprising a container, an aerosol generator connected to the container, wherein the container comprises a composition of any of aspects 31 to 42.
65. The aerosol delivery system of aspect 64, which is a nebulizer.
66. The nebulizer of aspect 65, which is a vibrating-mesh nebulizer.
67. The composition, container, kit, aerosol delivery system or nebulizer according to any of the preceding aspects for use in therapy.
68. The composition, container, kit, aerosol delivery system or nebulizer according to aspect 67, wherein the therapy is the treatment of respiratory disease.
69. Method for prevention and/or treatment of one or more diseases and/or disorders, comprising administering by aerosolization to a subject in need thereof a composition according to any of aspects 31 to 42.
70. Method of aspect 69, for prevention and/or treatment of one or more respiratory diseases, comprising administering by aerosolization to a subject in need thereof a composition according to any of aspects 31 to 42.
71. Method according to aspect 70, wherein the respiratory disease is RSV infection.
72. Method of any of aspects 69 to 71, wherein the composition is administered by nebulisation.
73. Method of aspect 72, wherein the composition is administered by a vibrating-mesh nebulizer.
74. Use of a composition, container, kit, aerosol delivery system or nebulizer according to any of the preceding aspects for the preparation of a medicament for treatment of respiratory diseases.
75. Use according to aspect 74, wherein the respiratory disease is RSV infection.

EXAMPLES

Example 1: Nebulizer Delivery of Nanobody P23IL0075

23IL0075 (SEQ ID NO: 1; EVQLLESGG-GLVQPGGSLRLSCAASGRIFSLPASGNIFNLL-TIAWYRQAPGKG RELVATINSGSRTYY-ADSVKGRFTISRDNSKKTLYLQMNSLRPEDTAVYYC QTSGSGSPNFWGQGTLVTVSSGGGG SGGG-SEVQLVESGGGLVQPGNSLRLS-CAASGFTFSSFGMSWVRQAPGKGLEWVSSIS-GSGSDTLYADSVKGRFTIS RDNAKTTLYLQMNSLRPEDTAVYYC-TIGGSLSRSSQGTLVTVSSGGGGSGGG-SEVQLLESGGGLVQPGGSLRLSCA ASGRTLSSYAMGWFRQAPGKGREFVARIS-QGGTAIYYADSVKGRFTISRDNSKNT-LYLQMNSLRPEDTAVYYCAKD PSPYYRGSAY-LLSGSYDSWGQGTLVTVSS) has been described as SEQ ID NO: 2622 in WO 2009/068627. 23IL0075 consists of three humanized variable domains of a heavy-chain llama antibody: 119A3v16 and 81A12v5 binding different epitopes of IL23 p19, and the ALB8 binding HSA. The subunits in both Nanobodies are fused head-to-tail with a 9G/S linker.

P23IL0075 was tested in the Omron pocket nebulizer MicroAIR belonging to the vibrating mesh nebulizers. In the device, P23IL0075 was tested at 4 mg/ml with a range of different formulation buffers. The stability of the samples to the nebulization process was tested by comparing pre- and post nebulization samples using size exclusion chromatography (SE-HPLC).

P23IL0075 was tested in PBS buffer (phosphate buffered saline)+0.01% Tween80, PBS+0.04% Tween80, 10 mM histidine pH6+10% sucrose+0.01% Tween 80 and 10 mM histidine pH6+10% sucrose+0.04% Tween 80. 0.5 ml of each solution was nebulized using the Omron pocket nebulizer MicroAIR. 5 microLiter of protein samples were injected onto the SE-HPLC (TSKgel G2000SWXL) column. The protein separation on SE-HPLC was performed at 0.2 ml/min for 70 minutes. 3.25 mM $Na_2HPO_4$+6.75 mM $NaH_2PO_4$+0.3M Arginine HCl+0.005% $NaN_3$ pH6 was used as mobile phase. The detection of eluting proteinaceous material was carried out by on-line detection by UV (Abs 280 nm).

The results in Table 1 show that the post-nebulization SE-HPLC profiles for all four different formulations tested presented a slight increased pre-peak as compared to the reference samples and indicate a minor increase in the relative amount of soluble aggregates. The recovery of the protein after nebulization was calculated from the total peak area of nebulized relative to reference sample. The results in Table 1 show that the nebulized samples formulated in histidine/sucrose have a comparable amount of P23IL0075 to the input material. This suggests that the material does not undergo significant degradation or fragmentation on nebulization.

Tween-80 increased the recovery and stabilizes P23IL0075 against aggregation and degradation in a dose-dependent manner. The recovery of the P23IL0075 Nanobody after nebulization was 100% in the histidine/sucrose formulation containing 0.04% Tween-80 and the lowest amount of soluble aggregates (3%) was observed. In a similar formulation containing only 0.01% Tween-80, recovery of P23IL0075 after nebulization was 90% and the percentage of soluble aggregates 4.8%. These data indicate Tween-80 has a stabilizing effect against aggregation after nebulization in a concentration dependent manner.

TABLE 1

Summary of the SE-HPLC analysis data of P23IL0075 at 4 mg/mL in different formulation buffers, after nebulization in an Omron pocket nebulizer MicroAIR compared to the reference samples (same formulation, no nebulization).

| Formulation Buffer | | Total Area | pre-peaks | main peak | post-peak | Recovery |
|---|---|---|---|---|---|---|
| PBS + 0.01% Tween80 | Reference | 131.5 | 0.4% | 95.2% | 4.4% | |
| | Nebulized | 91.4 | 5.2% | 89.4% | 5.4% | 70% |
| PBS + 0.04% Tween80 | Reference | 133.9 | 0.4% | 95.3% | 4.3% | |
| | Nebulized | 126.5 | 4.6% | 90.8% | 4.6% | 94% |
| 10 mM histidine pH 6 + 10% sucrose + 0.01% Tween80 | Reference | 135.4 | 0.8% | 99.2% | 0.0% | |
| | Nebulized | 121.3 | 4.8% | 95.2% | 0.0% | 90% |
| 10 mM histidine pH 6 + 10% sucrose + 0.04% Tween80 | Reference | 130.2 | 0.7% | 99.3% | 0.0% | |
| | Nebulized | 134.0 | 3.0% | 97.0% | 0.0% | 103% |

Example 2: Effect of Different Nebulizer Devices and Protein Concentrations on Nebulization of Nanobody RSV420

RSV 420 has the following sequence:
(SEQ ID NO: 3)
EVQLVESGGGLVQAGGSLSISCAASGGSLSNYVLGWFRQ
APGKEREFVAAINWRGDITIGPPNVEGRFTISRDNAKNTGYLQMNSLAPD
DTAVYYCGAGTPLNPGAYIYDWSYDYWGRGTQVTVSSGGGGSGGGGSGGG
GSEVQLVESGGGLVQAGGSLSISCAASGGSLSNYVLGWFRQAPGKEREFV
AAINWRGDITIGPPNVEGRFTISRDNAKNTGYLQMNSLAPDDTAVYYCGA
GTPLNPGAYIYDWSYDYWGRGTQVTVSSGGGGSGGGGSGGGGSEVQLVES
GGGLVQAGGSLSISCAASGGSLSNYVLGWFRQAPGKEREFVAAINWRGDI
TIGPPNVEGRFTISRDNAKNTGYLQMNSLAPDDTAVYYCGAGTPLNPGAY
IYDWSYDYWGRGTQVTVSS.

RSV 420 was tested in the AKITA® JET and AKITA$^2$ APIXNEB® nebulizers (Activaero) belonging to the jet and mesh nebulizers, respectively. In the devices, RSV 420 was tested at different concentrations (about 1, 5 and 20 mg/mL) in phosphate buffered saline (PBS) buffer. The stability of the samples to the nebulization process was tested by comparing pre- and post nebulization samples using size exclusion chromatography (SE-HPLC).

Each solution was nebulized as follow: the nebulizer was filled with 500 μl of liquid and the nebulized material was collected in a 50 ml polypropylene tube. 10 μg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

It was observed that nebulization, via mesh or jet nebulizer, induces discreet multimeric forms of RSV420, visible as pre-peaks when analyzed via SE-HPLC. Table 2 reports the integrations data from SE-HPLC analysis of samples after nebulization; in particular are shown the relative amounts of pre-peaks in SE-HPLC data (% oligomers) from different RSV420 concentrations (5.32 mg/ml and 22.90 mg/ml) nebulized using a jet (AKITA® JET) or mesh nebulizer (AKITA$^2$ APIXNEB®).

Each solution was nebulized as follow: the nebulizer was filled with 500 μl of liquid and the nebulized material was collected in a 50 ml polypropylene tube. 10 μg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

It was observed that nebulization, via mesh or jet nebulizer, induces discreet multimeric forms of RSV420, visible as pre-peaks when analyzed via SE-HPLC. Table 2 reports the integrations data from SE-HPLC analysis of samples after nebulization; in particular are shown the relative amounts of pre-peaks in SE-HPLC data (% oligomers) from different RSV420 concentrations (5.32 mg/ml and 22.90 mg/ml) nebulized using a jet (AKITA® JET) or mesh nebulizer (AKITA$^2$APIXNEB™).

From these results, it is clear that the amount of multimeric forms was much more pronounced when using a jet nebulizer (up to 45% of pre-peaks) compared to a mesh nebulizer; furthermore the formation of these side products was less pronounced when nebulizing solutions containing a higher concentration of protein. Specifically, when nebulizing a solution of RSV 420 at the concentration of about 20 mg/mL in PBS via a mesh nebulizer, the relative amount of pre-peaks visible by SE-HPLC analysis in the aerosol was at most 2%.

TABLE 2

Percentage oligomers (from SE-HPLC data) in nebulized RSV420 using different nebulizer devices and different protein concentrations

| Nebulizer type | Protein concentration [mg/mL] | % Oligomers |
|---|---|---|
| jet | 5.32 | 45 |
|  | 22.90 | 40 |
| mesh | 5.32 | 11 |
|  | 22.90 | 2 |

Example 3: Effect of Different Buffer/Excipient Combinations on Nebulization of Nanobody RSV434

RSV434 (SEQ ID NO: 2; DVQLVESGGGLVQAGGSL-SISCAASGGSLSNYVLGWFRQAPGKEREFVAA INWRGDITIGPPNVEGRFTISRD-NAKNTGYLQMNSLAPDDTAVYYCGAGTPLNPGAY-IYDWSYDYWGRGTQVTV SSGGGGSGGGGSGGGG-SEVQLVESGGGLVQAGGSLSISCAASGGSLSNYVLG WFRQAPGKEREFVAAINWRGDI TIGPPNVEGRFTIS-RDNAKNTGYLQMNSLAPDDTAVYYCGAGTPLNP-GAYIYDWSYDYWGRGTQVTVSSGGGGS GGGGSGGGGSEVQLVESGGGLVQAGGSLSIS-CAASGGSLSNYVLGWFRQAPGK-EREFVAAINWRGDITIGPPNVE GRFTISRD-NAKNTGYLQMNSLAPDDTAVYYCGAGTPLNPGAYI YDWSYDYWGRGTQVTVSS) has been described as SEQ ID NO: 142 in WO 2010/139808. RSV434 consists of three variable domains of a heavy-chain llama antibody. The subunits in both Nanobodies are fused head-to-tail with a 15G/S linker.

The stability of RSV434 was first analysed in buffer/excipient compositions showing a pH range from pH 3.8 to 7.0 by measuring the melting temperature (Tm) of RSV434 in the different compositions. This parameter, which defines a temperature at which 50% of the protein in solution is unfolded, is measured via differential scanning calorimetry (DSC) or thermal shift assay (TSA).

For the DSC experiments, all samples were brought to a concentration of 0.5 mg/mL in the buffers to be tested. The samples (400 μl) were applied to a 96-well plate and the DSC settings were as follows: final protein concentration 0.5 mg/mL; start temperature 35° C.; end temperature 95° C.; scan rate 1° C./min.; cooling rate: EXP; feedback mode: none; filtering period 4; pre-scan thermostat: 10 min.; post-scan thermostat: 0 min. Each analysis included also two buffer runs to establish stable baselines. The thermograms were obtained after subtraction of the baseline.

The DSC results indicated that Tm values were higher at neutral pHs (see Table 3).

TABLE 3

Tm determination via DSC of RSV 434 (0.5 mg/mL)
in different buffer/excipient compositions
(buffer concentration 20 mM)

| RSV 434 in | Melting temperature (° C.) |
|---|---|
| citrate pH 3.8 | 57.2 |
| acetate pH 3.8 | 57.3 |
| citrate + NaCl pH 5.5 | 64.7 |
| acetate + NaCl pH 5.5 | 64.8 |
| Bis-Tris pH 6.5 | 66.3 |
| Tris pH 7.0 | 66.6 |
| PBS | 67.0 |
| Na-phosphate pH 7.0 | 67.9 |

Next, the stability of RSV434 was analysed in selected buffer/excipient compositions in a pH range of 6.0 to 7.5 (see FIG. 1; all indicated buffers additionally contain 0.3 M mannitol) by measuring the melting temperature (Tm) of RSV434 in the different buffers via thermal shift assay (TSA).

The thermal shift assay (TSA) can be performed in a high-throughput manner (96-well plate) in a Q-PCR device to evaluate the effect of buffer (couple), ionic strength, pH and excipients on the thermal stability of proteins. The assay results in a Tm value that is indicative for the thermal stability in the tested buffers. Briefly, the assay follows the signal changes of a fluorescence dye, such as Sypro Orange, while the protein undergoes thermal unfolding. When Sypro Orange is added to a properly folded protein solution, it is exposed in an aqueous environment and its fluorescence signal is quenched. When the temperature rises, the protein undergoes thermal unfolding and exposes its hydrophobic core region. Sypro Orange then binds to the hydrophobic regions and unquenches, which results in the increase of the fluorescence signal. The assay was performed on solutions containing the buffer to be tested, the protein sample at 0.1 mg/mL and 10× Sypro Orange. The program consisted of the following steps: heat to 37° C. at a ramp rate of 4.4° C./s and hold for 10 s; heat to 90° C. at a continuous ramp rate of 0.01° C./s (66 acquisitions per ° C.); and cool to 37° C. at a ramp rate of 2.2° C./s and hold for 10 s.

In addition, the effect of different buffer/excipient compositions on the stability of RSV434 was further analysed upon nebulization by SE-HPLC.

5 mg/ml solutions of Nanobody RSV434 were nebulized via the handheld mesh nebulizer Omron MicroAir in the presence of different excipients. Samples before and after nebulization were then analyzed via size exclusion chromatography.

Figure 2:
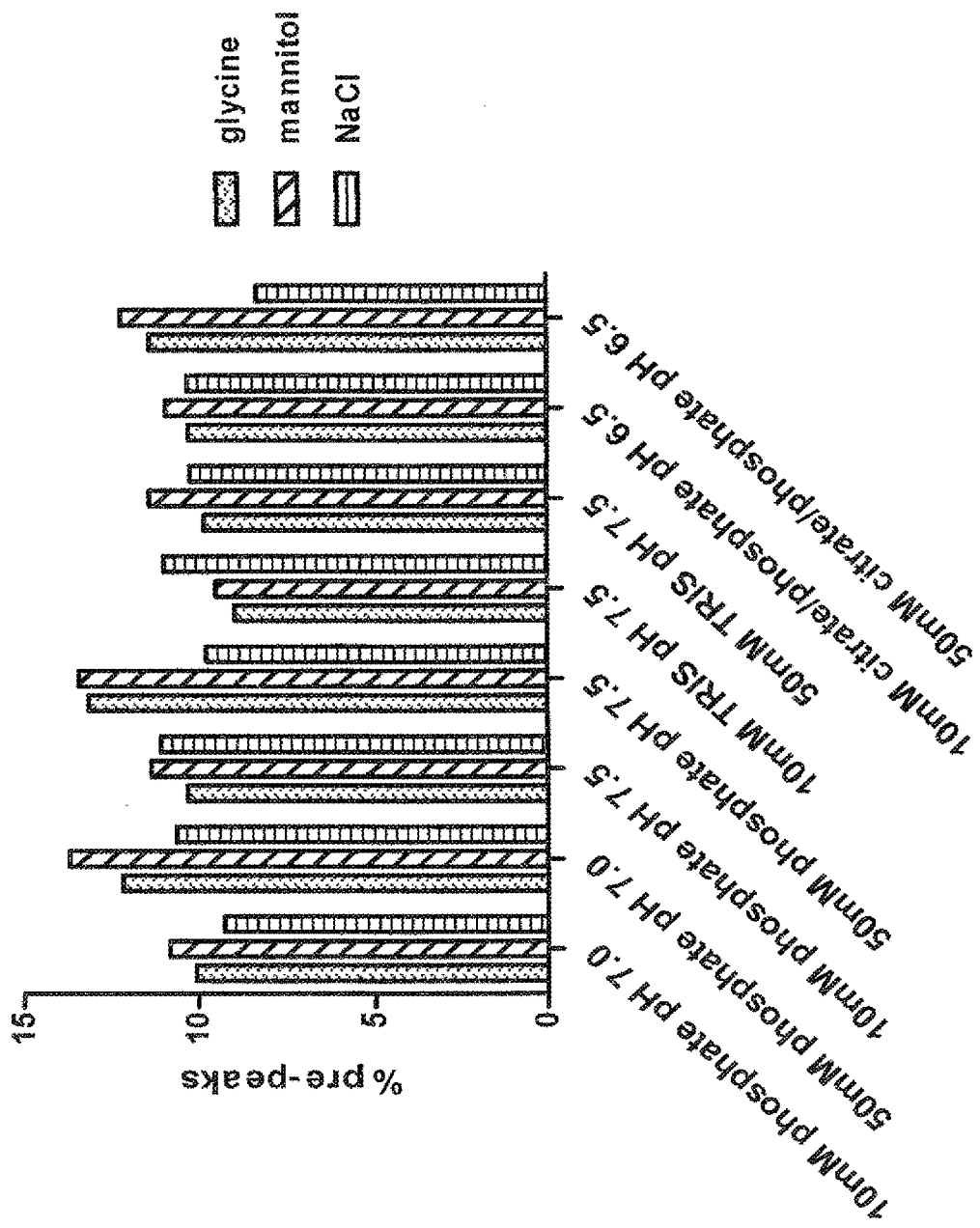
FIG. 2. Percentage (%) of pre-peaks measured by SE-HPLC analysis of nebulized RSV434 at 5 mg/mL via the Omron mesh nebulizer in the presence of different buffer/excipient compositions (glycine According to the European Pharmacopoeia, a solution is considered "isotonic" if it has an osmolality of 290±30 mOsm/kg. Isotonicity can be measured by, for example, a vapor pressure or ice-freezing type osmometer.

Briefly, RSV434 was formulated at 5 mg/ml in the following buffers: 10 mM sodium phosphate pH 7.0, 50 mM sodium phosphate pH 7.0, 10 mM phosphate pH 7.5, 50 mM phosphate pH 7.5, 10 mM TRIS pH 7.5, 50 mM TRIS pH 7.5, 10 mM citrate/phosphate pH 6.5, 50 mM citrate/phosphate pH 6.5. To each solution was also added, as osmolarity agent, glycine or mannitol to a final concentration of 0.3 M, or sodium chloride to a final concentration of 0.15 M (see Table 4 and FIG. 2). Each solution was nebulized as follow: the nebulizer was filled with 500 µl of liquid and the nebulized material was collected in a 50 ml polypropylene tube. 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Table 4 reports the integration data from SE-HPLC analysis of samples before and after nebulization; in particular are shown the relative amounts of pre- and post peaks, as well as the product main peak. It has been observed that nebulization, via mesh or jet nebulizer, induces discreet multimeric forms of RSV434, probably due to molecules exposure to the air-water interface during the aerosolization process. The total amount of pre-peaks represents the formation of such multimeric forms. The total recovery column reports the percentage of material recovered after nebulization based on the ratio of total area after and before nebulization.

From these results, it is clear that the amount of multimeric forms is above 10% in most of the conditions tested; a few buffer/excipient compositions lead to a lower multimerization, such as, for example, 10 mM sodium phosphate pH 7.0/0.15 M NaCl, 50 mM phosphate pH 7.5/0.15 M NaCl, 10 mM TRIS pH 7.5/0.3 M glycine, 50 mM TRIS pH 7.5/0.3 M glycine, 50 mM citrate/phosphate pH 6.5/0.15 M NaCl. In terms of protein recovery, all the combinations containing TRIS have a better behavior.

TABLE 4

Summary of the SE-HPLC analyses data of RSV434 at 5 mg/mL in different formulation
buffers, after nebulization via Omron pocket nebulizer MicroAIR (nebulized) compared to the non-
nebulized material (REF)

| RSV434 5 mg/ml | | pre-peak 1 | pre-peak 2 | pre-peak 3 | pre-peak 4 | main peak | post-peak 1 | total recovery | total % pre-peak |
|---|---|---|---|---|---|---|---|---|---|
| 10 mM phosphate pH 7.0 0.3M glycine | REF | 0.12% | 0.06% | 0.34% | 3.90% | 95.48% | 0.10% | | 0.53% |
| | nebulized | 3.38% | 2.32% | 4.39% | 3.50% | 86.37% | 0.05% | 86.59% | 10.09% |
| 10 mM phosphate pH 7.0 0.3M mannitol | REF | 0.16% | 0.09% | 0.23% | 4.30% | 95.10% | 0.12% | | 0.48% |
| | nebulized | 3.90% | 2.40% | 4.56% | 3.73% | 85.34% | 0.08% | 86.41% | 10.85% |
| 10 mM phosphate pH 7.0 0.15M NaCl | REF | 0.08% | 0.00% | 0.15% | 3.69% | 95.86% | 0.22% | | 0.24% |
| | nebulized | 3.26% | 1.95% | 4.06% | 3.33% | 87.16% | 0.23% | 82.76% | 9.27% |
| 50 mM phosphate pH 7.0 0.3M glycine | REF | 0.10% | 0.01% | 0.05% | 4.38% | 95.28% | 0.18% | | 0.16% |
| | nebulized | 5.14% | 2.43% | 4.60% | 3.65% | 84.01% | 0.16% | 79.75% | 12.17% |
| 50 mM phosphate pH 7.0 0.3M mannitol | REF | 0.24% | 0.04% | 0.17% | 4.41% | 95.02% | 0.12% | | 0.45% |
| | nebulized | 6.15% | 2.64% | 4.92% | 3.76% | 82.42% | 0.11% | 90.41% | 13.71% |
| 50 mM phosphate pH 7.0 0.15M NaCl | REF | 0.14% | 0.07% | 0.00% | 3.97% | 95.68% | 0.15% | | 0.21% |
| | nebulized | 3.98% | 2.18% | 4.50% | 3.37% | 85.82% | 0.16% | 80.11% | 10.66% |
| 10 mM phosphate pH 7.5 0.3M glycine | REF | 0.01% | 0.01% | 0.05% | 3.84% | 96.01% | 0.07% | | 0.07% |
| | nebulized | 3.48% | 2.38% | 4.46% | 3.41% | 86.21% | 0.06% | 91.24% | 10.33% |
| 10 mM phosphate pH 7.5 0.3M mannitol | REF | 0.02% | 0.08% | 0.25% | 4.42% | 95.10% | 0.14% | | 0.34% |
| | nebulized | 4.14% | 2.51% | 4.70% | 3.76% | 84.78% | 0.10% | 91.07% | 11.36% |
| 10 mM phosphate pH 7.5 0.15M NaCl | REF | 0.05% | 0.01% | 0.14% | 3.79% | 95.76% | 0.25% | | 0.20% |
| | nebulized | 4.08% | 2.33% | 4.69% | 3.39% | 85.29% | 0.23% | 91.34% | 11.09% |

TABLE 4-continued

Summary of the SE-HPLC analyses data of RSV434 at 5 mg/mL in different formulation buffers, after nebulization via Omron pocket nebulizer MicroAIR (nebulized) compared to the non-nebulized material (REF)

| RSV434 5 mg/ml | | pre-peak 1 | pre-peak 2 | pre-peak 3 | pre-peak 4 | main peak | post-peak 1 | total recovery | total % pre-peak |
|---|---|---|---|---|---|---|---|---|---|
| 50 mM phosphate pH 7.5 | REF | 0.15% | 0.02% | 0.06% | 4.22% | 95.39% | 0.17% | | 0.22% |
| 0.3M glycine | nebulized | 5.61% | 2.62% | 4.91% | 3.68% | 83.01% | 0.16% | 88.90% | 13.15% |
| 50 mM phosphate pH 7.5 | REF | 0.09% | 0.01% | 0.08% | 4.25% | 95.46% | 0.12% | | 0.18% |
| 0.3M mannitol | nebulized | 6.07% | 2.58% | 4.78% | 3.84% | 82.65% | 0.08% | 92.67% | 13.43% |
| 50 mM phosphate pH 7.5 | REF | 0.08% | 0.06% | 0.03% | 3.98% | 95.70% | 0.15% | | 0.17% |
| 0.15M NaCl | nebulized | 3.43% | 2.02% | 4.32% | 3.37% | 86.74% | 0.13% | 88.68% | 9.77% |
| 10 mM TRIS pH 7.5 | REF | 0.04% | 0.04% | 0.00% | 3.81% | 96.05% | 0.05% | | 0.08% |
| 0.3M glycine | nebulized | 2.78% | 2.11% | 4.08% | 3.35% | 87.67% | 0.02% | 94.81% | 8.97% |
| 10 mM TRIS pH 7.5 | REF | 0.08% | 0.06% | 0.21% | 4.28% | 95.26% | 0.10% | | 0.36% |
| 0.3M mannitol | nebulized | 3.16% | 2.18% | 4.17% | 3.72% | 86.71% | 0.06% | 94.06% | 9.51% |
| 10 mM TRIS pH 7.5 | REF | 0.07% | 0.01% | 0.09% | 3.86% | 95.74% | 0.24% | | 0.17% |
| 0.15M NaCl | nebulized | 3.85% | 2.32% | 4.83% | 3.19% | 85.60% | 0.22% | 93.68% | 11.00% |
| 50 mM TRIS pH 7.5 | REF | 0.02% | 0.04% | 0.05% | 3.86% | 95.89% | 0.14% | | 0.11% |
| 0.3M glycine | nebulized | 3.49% | 2.14% | 4.20% | 3.43% | 86.60% | 0.14% | 96.31% | 9.83% |
| 50 mM TRIS pH 7.5 | REF | 0.19% | 0.08% | 0.27% | 4.50% | 94.75% | 0.21% | | 0.54% |
| 0.3M mannitol | nebulized | 4.44% | 2.41% | 4.55% | 3.75% | 84.63% | 0.22% | 95.15% | 11.40% |
| 50 mM TRIS pH 7.5 | REF | 0.11% | 0.01% | 0.13% | 3.64% | 95.86% | 0.26% | | 0.25% |
| 0.15M NaCl | nebulized | 3.40% | 2.18% | 4.67% | 3.23% | 86.31% | 0.22% | 95.17% | 10.24% |
| 10 mM citrate/phosphate pH 6.5 | REF | 0.21% | 0.02% | 0.40% | 3.98% | 95.29% | 0.10% | | 0.63% |
| 0.3M glycine | nebulized | 4.18% | 2.12% | 3.99% | 3.60% | 86.06% | 0.05% | 91.51% | 10.29% |
| 10 mM citrate/phosphate pH 6.5 | REF | 0.35% | 0.06% | 0.22% | 4.26% | 94.97% | 0.15% | | 0.62% |
| 0.3M mannitol | nebulized | 4.64% | 2.22% | 4.09% | 4.02% | 84.93% | 0.10% | 90.77% | 10.95% |
| 10 mM citrate/phosphate pH 6.5 | REF | 0.01% | 0.03% | 0.09% | 3.75% | 95.91% | 0.21% | | 0.14% |
| 0.15M NaCl | nebulized | 4.25% | 2.00% | 4.08% | 3.53% | 85.91% | 0.24% | 92.33% | 10.33% |
| 50 mM citrate/phosphate pH 6.5 | REF | 0.05% | 0.09% | 0.06% | 4.13% | 95.55% | 0.12% | | 0.20% |
| 0.3M glycine | nebulized | 5.24% | 2.06% | 4.09% | 3.80% | 84.71% | 0.10% | 91.71% | 11.39% |
| 50 mM citrate/phosphate pH 6.5 | REF | 0.18% | 0.02% | 0.07% | 4.21% | 95.36% | 0.16% | | 0.26% |
| 0.3M mannitol | nebulized | 5.60% | 2.26% | 4.36% | 3.90% | 83.73% | 0.15% | 93.57% | 12.22% |
| 50 mM citrate/phosphate pH 6.5 | REF | 0.19% | 0.08% | 0.01% | 3.81% | 95.74% | 0.17% | | 0.28% |
| 0.15M NaCl | nebulized | 2.95% | 1.67% | 3.71% | 3.60% | 87.90% | 0.18% | 85.88% | 8.33% |

Example 4: Effect of Surfactants and Selected Buffer/Excipient Compositions on Nebulization of Nanobody RSV434

5 mg/ml solutions of Nanobody RSV434 were nebulized via the handheld mesh nebulizer Omron MicroAir in the presence of selected buffers and surfactants. Samples before and after nebulization were then analyzed via size exclusion chromatography.

In a first series of experiments, RSV434 was formulated at 5 mg/ml in the following buffers: 0.9% NaCl (saline), 10 mM TRIS pH 7.5/0.3 M glycine, 10 mM sodium phosphate pH 7.5/0.15 M NaCl, 50 mM citrate/phosphate pH 6.5/0.15 M NaCl. In a second series of experiments, RSV434 was formulated at 5 mg/ml in the following buffers: 0.9% NaCl (saline), PBS, 10 mM sodium phosphate pH 7.0/0.14 M NaCl, 10 mM sodium phosphate pH 7.5/0.145 M NaCl, 10 mM citrate/phosphate pH 6.5/0.133 M NaCl. Each of these buffer conditions was tested without or with the addition of 0.04% polysorbate 80 (Tween 80) and/or 0.02% polyethylene glycol (PEG) 1000. Each solution was nebulized as follow: the nebulizer was filled with 500 µl of liquid and the nebulized material was collected in a 50 ml polypropylene tube. 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Figure 3:
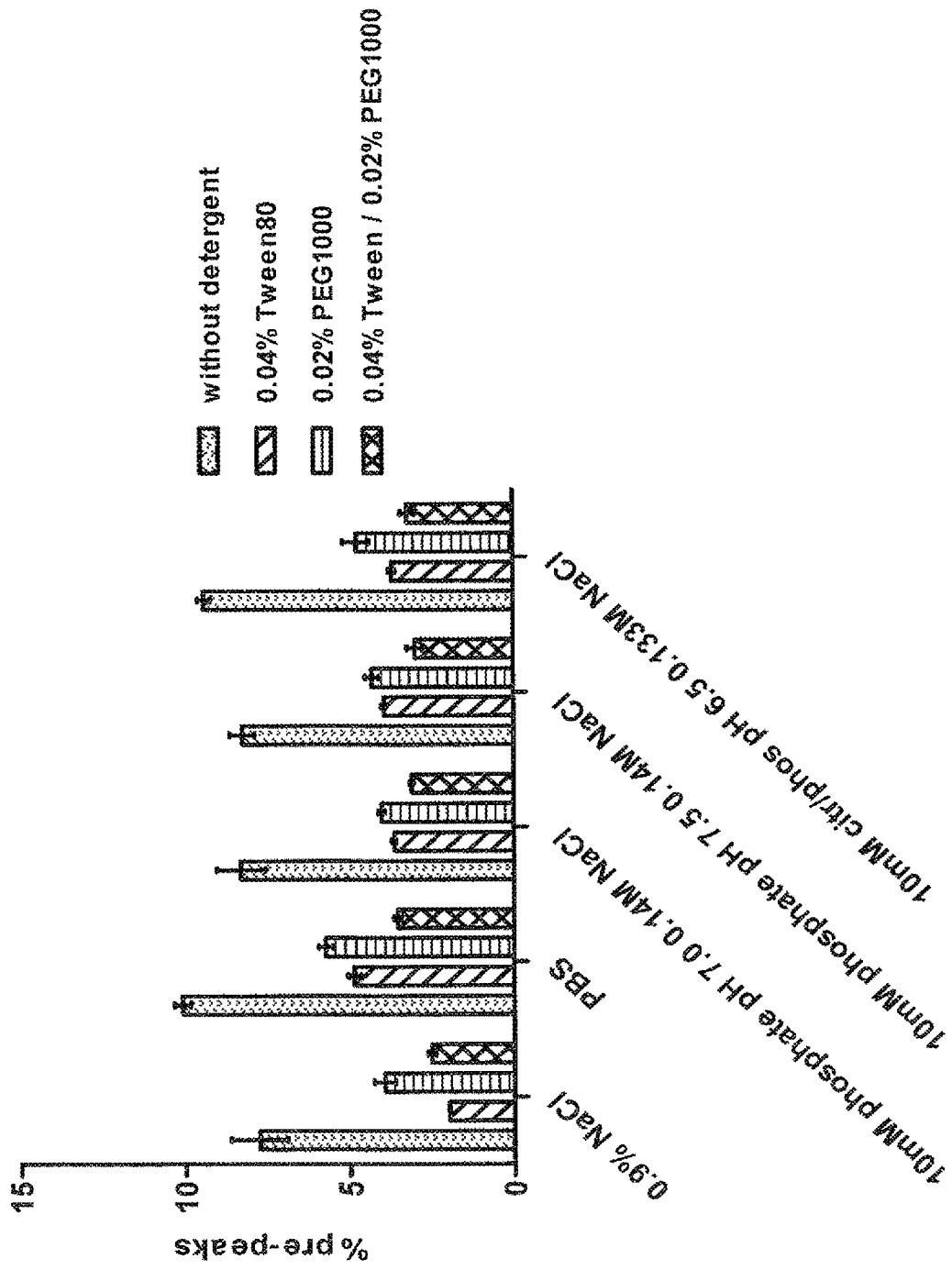

Table 5 reports the integrations data from SE-HPLC analysis of samples from the first series of experiments before and after nebulization; in particular are shown the relative amounts of pre- and post peaks, as well as the product main peak. The total amount of pre-peaks represents the formation of multimeric forms. The total recovery column reports the percentage of material recovered after nebulization based on the ratio of total area after and before nebulization. FIG. 3 shows the percentage of pre-peaks measured by SE-HPLC analysis of samples from the second series of experiments after nebulization.

From the reported results, the beneficial effect on reducing the amount of multimeric material after nebulization is clear for both Tween 80 and PEG 1000. In the case of saline and 50 mM citrate/phosphate pH 6.5/0.15 M NaCl solutions, Tween 80 appears to have a better behavior. On the other side, PEG 1000 seems always to increase the protein recovery after nebulization.

TABLE 5

Summary of the SE-HPLC analyses data of RSV434 at 5 mg/mL in different formulation buffers after nebulization via Omron pocket nebulizer MicroAIR (nebulized) compared to the non-nebulized (REF) material.

| RSV434 5 mg/ml | Surfactant | | pre-peak 1 | pre-peak 2 | pre-peak 3 | pre-peak 4 | main peak | post-peak 1 | total recovery | total % pre-peak |
|---|---|---|---|---|---|---|---|---|---|---|
| 0.9% NaCl | / | REF | 0.06% | 0.05% | 0.38% | 3.93% | 95.30% | 0.28% | 100.00% | 0.49% |
| | | nebulized | 1.81% | 1.40% | 3.28% | 3.45% | 89.73% | 0.32% | 85.17% | 6.50% |
| | 0.04% Tween80 | REF | 0.06% | 0.01% | 0.20% | 3.96% | 95.47% | 0.30% | 100.00% | 0.26% |
| | | nebulized | 0.58% | 0.29% | 1.50% | 3.79% | 93.50% | 0.33% | 81.96% | 2.38% |
| | 0.02% PEG1000 | REF | 0.07% | 0.03% | 0.03% | 3.92% | 95.67% | 0.29% | 100.00% | 0.13% |
| | | nebulized | 1.34% | 0.97% | 2.29% | 3.56% | 91.55% | 0.29% | 91.18% | 4.60% |
| 10 mM TRIS pH 7.5 | / | REF | 0.06% | 0.01% | 0.10% | 4.01% | 95.79% | 0.03% | 100.00% | 0.18% |
| | | nebulized | 2.60% | 2.02% | 3.90% | 3.67% | 87.80% | 0.00% | 93.53% | 8.52% |
| 0.3M glycine | 0.04% Tween80 | REF | 0.13% | 0.01% | 0.16% | 4.22% | 95.31% | 0.18% | 100.00% | 0.30% |
| | | nebulized | 0.45% | 0.71% | 2.40% | 4.11% | 92.17% | 0.16% | 95.80% | 3.56% |
| | 0.02% PEG1000 | REF | 0.15% | 0.04% | 0.02% | 4.11% | 95.65% | 0.03% | 100.00% | 0.21% |
| | | nebulized | 0.77% | 0.85% | 1.83% | 3.77% | 92.78% | 0.01% | 92.90% | 3.45% |
| 10 mM phosphate pH 7.0 0.15M NaCl | / | REF | 0.02% | 0.01% | 0.17% | 3.95% | 95.57% | 0.28% | 100.00% | 0.20% |
| | | nebulized | 3.58% | 2.18% | 4.57% | 3.47% | 85.90% | 0.29% | 93.80% | 10.33% |
| | 0.04% Tween80 | REF | 0.14% | 0.03% | 0.21% | 3.97% | 95.36% | 0.29% | 100.00% | 0.38% |
| | | nebulized | 2.09% | 0.74% | 2.54% | 3.76% | 90.55% | 0.32% | 89.50% | 5.37% |
| | 0.02% PEG1000 | REF | 0.02% | 0.03% | 0.14% | 3.98% | 95.55% | 0.29% | 100.00% | 0.18% |
| | | nebulized | 1.61% | 1.17% | 2.65% | 3.53% | 90.77% | 0.27% | 94.31% | 5.43% |
| 50 mM citrate/ phosphate pH 6.5 0.15M NaCl | / | REF | 0.24% | 0.07% | 0.03% | 4.06% | 95.45% | 0.15% | 100.00% | 0.34% |
| | | nebulized | 3.19% | 1.97% | 4.29% | 3.60% | 86.80% | 0.16% | 85.43% | 9.45% |
| | 0.04% Tween80 | REF | 0.10% | 0.03% | 0.13% | 4.24% | 95.34% | 0.17% | 100.00% | 0.26% |
| | | nebulized | 0.52% | 0.29% | 1.50% | 4.00% | 93.48% | 0.20% | 85.37% | 2.32% |
| | 0.02% PEG1000 | REF | 0.18% | 0.07% | 0.03% | 4.02% | 95.55% | 0.15% | 100.00% | 0.29% |
| | | nebulized | 0.70% | 0.72% | 1.94% | 3.67% | 92.81% | 0.16% | 87.92% | 3.36% |

Example 5: Effect of Different Concentrations of Polysorbate (Tween) 80 on Nebulization of Nanobody RSV434

5 mg/ml solutions of Nanobody RSV434 were nebulized via the mesh nebulizer Akita APIXNEB® (Activaero) in the presence of selected buffers and surfactants. Samples before and after nebulization were then analyzed via size exclusion chromatography.

Briefly, RSV 434 was formulated at 5 mg/ml in 10 mM sodium phosphate pH 7.5/0.14 M NaCl in the presence of different concentrations of Tween 80 (0, 0.005%, 0.01%, 0.02%, 0.04%, 0.08%). Each solution was nebulized as follow: the nebulizer was filled with 500 µl of liquid and the nebulized material was collected in a 50 ml polypropylene tube; each formulation condition was tested in triplicate. 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Figure 4:
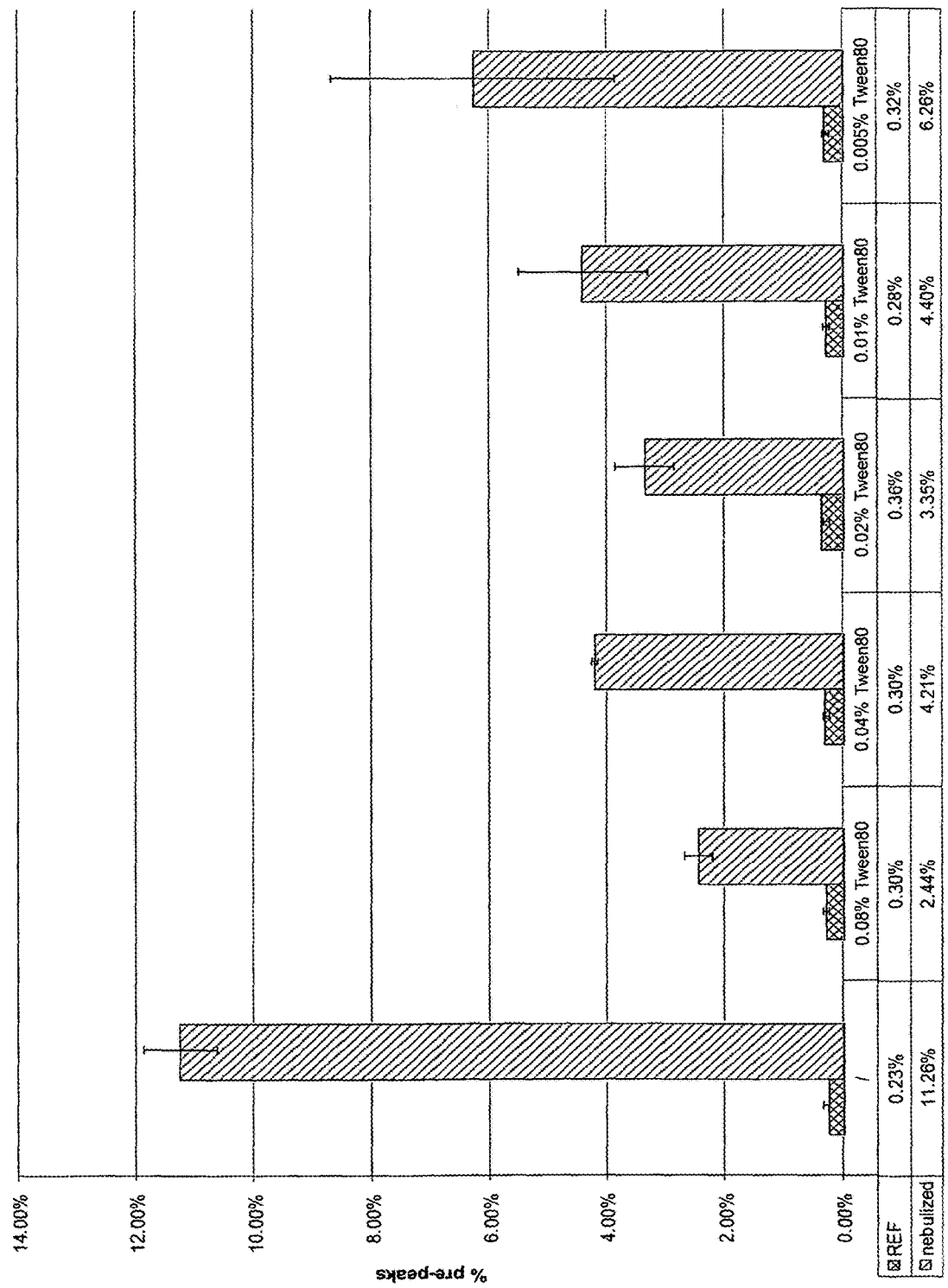
Figure 5:
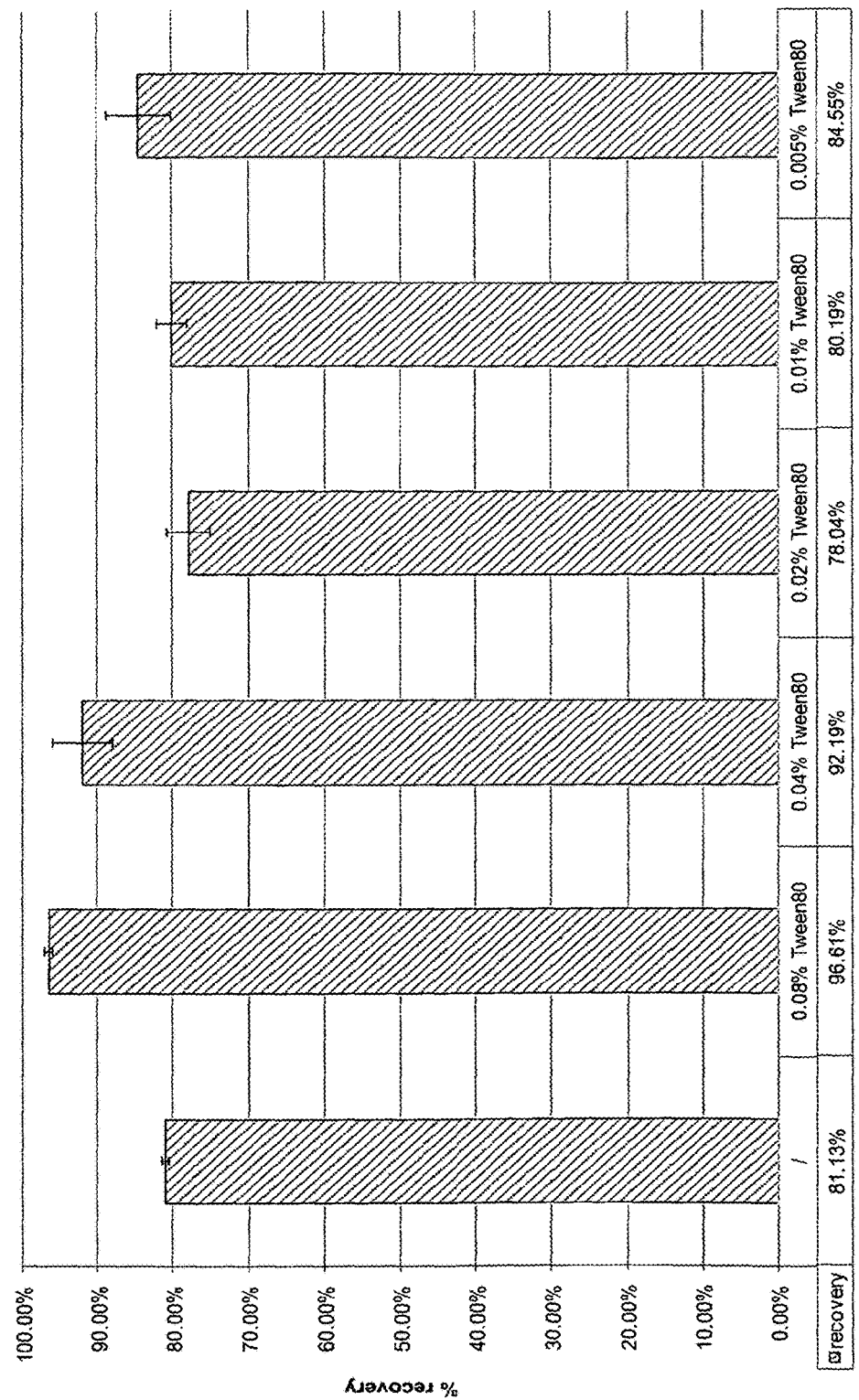

FIG. 4 reports the relative amount of pre-peaks obtained from SE-HPLC analysis of samples before and after nebulization. The total amount of pre-peaks represents the formation of multimeric forms. FIG. 5 shows the effect of Tween 80 on total protein recovery based on SE-HPLC analysis of samples before and after nebulization.

From the data obtained it can be concluded that relative amount of multimeric forms after nebulization via mesh nebulizer is dependent on the concentration of detergent (specifically Tween 80) in the starting solution. The use of 0.08% Tween 80 gives place to the lowest percentage of pre-peaks (FIG. 4) and the highest area recovery (FIG. 5).

The highest protein recovery is obtained with nebulizing solutions containing 0.08% or 0.04% Tween 80.

Example 6: Effect of Different Concentrations of Polyethylene Glycol (PEG) 1000 and Pluronic F68 (Poloxamer 188; Lutrol F68) on Nebulization of Nanobody RSV434

5 mg/ml solutions of Nanobody RSV434 were nebulized via the mesh nebulizer Akita APIXNEB® (Activaero) in the presence of selected buffers and surfactants. Samples before and after nebulization were then analyzed via size exclusion chromatography.

Briefly, RSV434 was formulated at 5 mg/ml in 10 mM sodium phosphate pH 7.0/0.13 M NaCl in the presence of different concentrations of PEG 1000 (0.02%, 0.04%) or Pluronic F68 (0.001%, 0.02%, 0.04%). Each solution was nebulized as follow: the nebulizer was filled with 500 µl of liquid and the nebulized material was collected in a 50 ml polypropylene tube; 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Table 6 reports the integration data from SE-HPLC analysis of samples before and after nebulization; in particular are shown the relative amounts of pre-peaks, as well as the product main peak. The total amount of pre-peaks represents the formation of multimeric forms. The total recovery column reports the percentage of material recovered after nebulization based on the ratio of total area after and before nebulization. As reference are reported data from a previous experiment conducted in the same experimental conditions, using a solution of RSV434 in 10 mM sodium phosphate pH 7.0/0.14 M NaCl, without the addition of surfactants.

The data clearly show the beneficial role of PEG 1000 at the concentration of 0.04% and especially of Pluronic F-68 at the concentration of 0.04% in reducing the formation of multimeric forms after nebulization via a mesh nebulizer. The same excipients also allow a higher recovery of material after the same process.

TABLE 1

Summary of the SE-HPLC analyses data of 5 mg/ml solutions of RSV434 with different excipients after nebulization via Akita APIXNEB ® nebulizer (nebulized) compared to the non-nebulized material (REF).

| Surfactant | | pre-peak 1 | pre-peak 2 | pre-peak 3 | main peak | % Total recovery | total % pre-peak |
|---|---|---|---|---|---|---|---|
| 0.04% PF-68 | REF | 0.04% | 0.02% | 0.09% | 99.86% | | 0.14% |
| | nebulized | 0.57% | 0.41% | 1.24% | 97.78% | 87.36% | 2.22% |
| 0.02% PF-68 | REF | 0.04% | 0.01% | 0.10% | 99.85% | | 0.15% |
| | nebulized | 1.79% | 1.01% | 2.50% | 94.70% | 90.20% | 5.30% |
| 0.01% PF-68 | REF | 0.11% | 0.04% | 0.15% | 99.71% | | 0.29% |
| | nebulized | 3.46% | 1.78% | 3.87% | 90.89% | 86.93% | 9.11% |
| 0.04% PEG1000 | REF | 0.08% | 0.04% | 0.10% | 99.77% | | 0.23% |
| | nebulized | 1.39% | 0.76% | 1.82% | 96.03% | 91.98% | 3.97% |
| 0.02% PEG1000 | REF | 0.13% | 0.04% | 0.15% | 99.68% | | 0.32% |
| | nebulized | 2.68% | 1.39% | 3.02% | 92.91% | 100.44% | 7.09% |
| ref. no surfactant | REF | 0.08% | 0.05% | 0.30% | 95.15% | | 0.43% |
| | nebulized | 2.95% | 1.62% | 3.42% | 88.07% | 79.52% | 7.99% |

Example 7: Effect of Polyethylene Glycol (PEG) 1000, Pluronic F68 (Poloxamer 188; Lutrol F68) and Polysorbate (Tween) 80 on Nebulization of Nanobody RSV434 Via a Jet Nebulizer 5 mg/ml solutions of Nanobody RSV434 were nebulized via the jet nebulizer AkitaJet (Activaero) in the presence of selected surfactants. Samples before and after nebulization were then analyzed via size exclusion chromatography.

Briefly, RSV434 was formulated at 5 mg/ml in 10 mM sodium phosphate pH 7.0/0.13 M NaCl in the presence of PEG 1000 (0.04%), Pluronic F68 (0.04%) or Tween 80 (0.04%, 0.08%). Each solution was nebulized as follow: the nebulizer was filled with 2 ml of liquid and the nebulized material was collected via an impinger containing 30 ml of PBS; after nebulization the solution was collected from the impinger and diluted to 50 ml; protein concentration was determined via OD280 measurement and 10 µg of each sample before and after nebulization was analyzed via SE-HPLC using a TSK Gel SuperSW3000 (flow rate 0.15 ml/min, run time 35 minutes, mobile phase 3.9 mM KH2PO4+6.1 mM Na2HPO4+0.4 M NaCl pH 7.0; detection was set at 280 nm).

Table 7 reports the integration data results from SE-HPLC analysis of samples before and after nebulization; in particular are shown the relative amounts of pre-peaks, as well as the product (main peak) purity. The total amount of pre-peaks represents the formation of multimeric forms.

It appears that PEG 1000 at the concentration of 0.04% and Pluronic F-68 at the concentration of 0.04% reduce the formation of multimeric forms after nebulization also in case of nebulization via a jet nebulizer but not in a relevant manner. The use of Tween 80 seems to be more efficient for this purpose; the use of a higher surfactant concentration (0.08% instead of 0.04%) does not lead to an important decrease in the formation of higher molecular weight forms (pre-peaks).

TABLE 7

Summary of the SE-HPLC analyses data of 5 mg/ml solutions of RSV434 with different excipients after nebulization via AkitaJet nebulizer (nebulized) compared to the non-nebulized material (REF).

| Surfactant | | pre-peak 1 | pre-peak 2 | pre-peak 3 | main peak | total % pre-peak |
|---|---|---|---|---|---|---|
| 0.04% PEG1000 | REF | 0.20% | 0.00% | 0.30% | 99.40% | 0.50% |
| | nebulized | 11.85% | 8.80% | 19.00% | 60.20% | 39.65% |
| 0.04% PF-68 | REF | 0.24% | 0.01% | 0.21% | 99.32% | 0.46% |
| | nebulized | 9.72% | 7.47% | 16.85% | 65.75% | 34.04% |
| 0.04% Tween80 | REF | 0.20% | 0.00% | 0.40% | 99.30% | 0.60% |
| | nebulized | 5.37% | 3.84% | 14.60% | 75.90% | 23.81% |
| 0.08% Tween80 | REF | 0.10% | 0.00% | 0.30% | 99.30% | 0.40% |
| | nebulized | 4.10% | 3.30% | 12.45% | 79.75% | 19.85% |
| ref. no surfactant | REF | 0.08% | 0.06% | 0.46% | 99.27% | 0.60% |
| | nebulized | 14.42% | 8.96% | 19.81% | 56.70% | 43.19% |

Example 8: Effect of Protein Concentration on Nebulization of Nanobody RSV434

Solutions of Nanobody RSV434 at 3 different concentrations were nebulized via the mesh nebulizer Akita APIXNEB® (Activaero) in the presence of selected buffers and Tween 80 as surfactants. Samples before and after nebulization were then analyzed via size exclusion chromatography.

Briefly, RSV434 was formulated at 5 mg/ml, 25 mg/ml and 50 mg/ml in saline (0.9% NaCl) or in PBS (phosphate buffered saline), with or without the presence of 0.04% Tween 80.

Each solution was nebulized as follows: the nebulizer was filled with 500 µl of liquid and the nebulized material was collected in a 50 ml polypropylene tube; 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Figure 6:
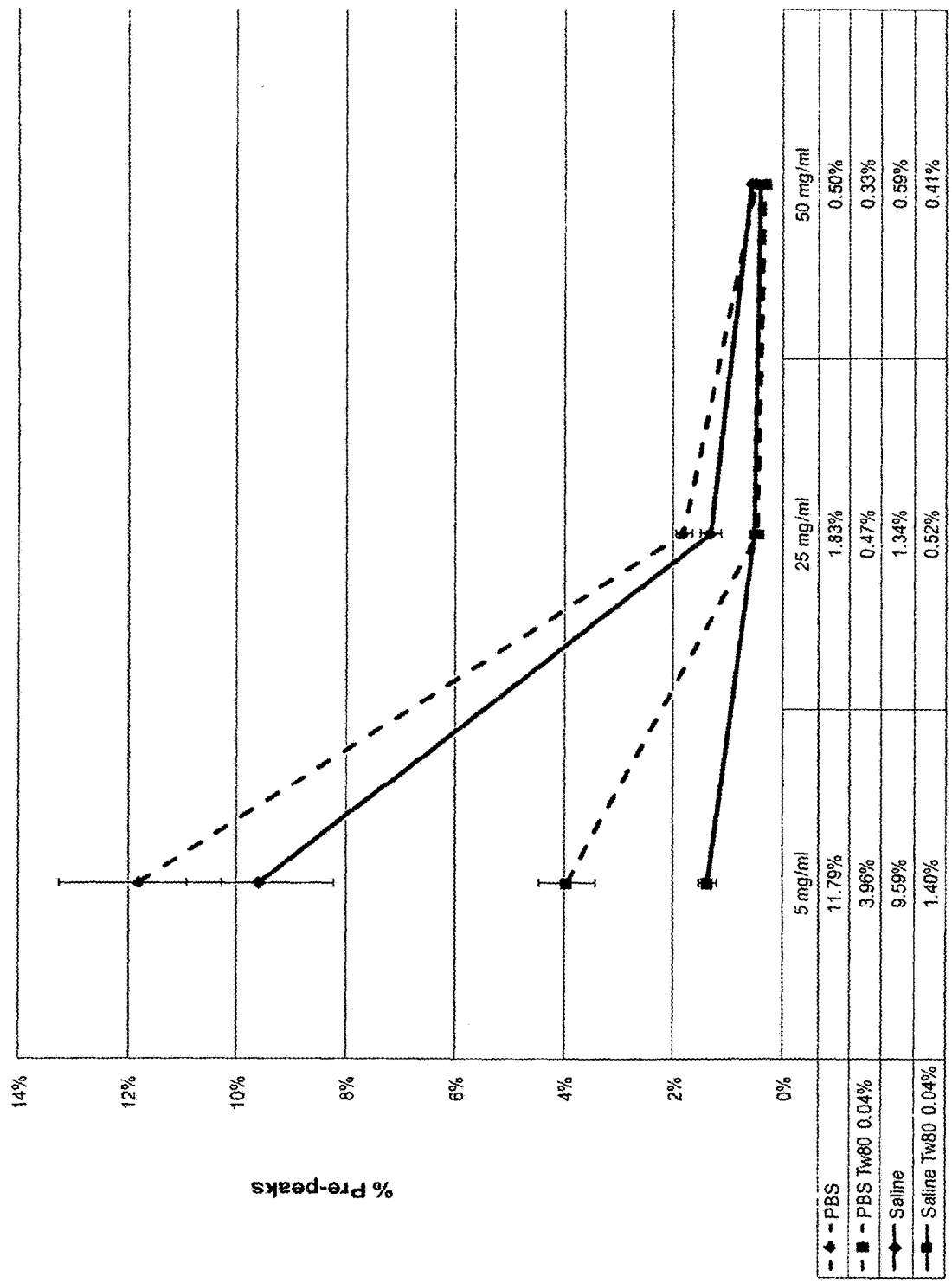

FIG. 6 reports the relative amount of pre-peaks obtained from SE-HPLC analysis of samples after nebulization. The total amount of pre-peaks represents the formation of multimeric forms. It is clear how the formation of multimeric forms of RSV434 is inversely related to the concentration of the protein. At higher protein concentrations (25 and 50 mg/ml) the effect of buffer and surfactant on the multimer formation appears negligible.

Example 9: Effect of Protein Concentration on Nebulization of Nanobody RSV434 Via a Jet Nebulizer Solutions of Nanobody RSV434 at 3 different concentrations were nebulized via the jet nebulizer AkitaJet (Activaero) in the presence of selected buffers and Tween 80 as surfactant. Samples before and after nebulization were then analyzed via size exclusion chromatography.

Briefly, RSV 434 was formulated at 5 mg/ml, 25 mg/ml and 50 mg/ml in 10 mM sodium phosphate (NaH2PO4/Na2HPO4)+0.13 M NaCl pH 7.0 or in PBS (phosphate buffered saline), with or without the presence of 0.04% Tween 80.

Each solution was nebulized as follow: the nebulizer was filled with 2 ml of liquid and the nebulized material was collected via an impinger containing 30 ml of PBS; after nebulization the solution was collected from the impinger and diluted to 50 ml; protein concentration was determined via OD280 measurement and 10 µg of each sample before and after nebulization were analyzed via SE-HPLC using a TSK Gel SuperSW3000 (flow rate 0.15 ml/min, run time 35 minutes, mobile phase 3.9 mM $KH_2PO_4$+6.1 mM $Na_2HPO_4$+0.4 M NaCl pH 7.0; detection was set at 280 nm).

Figure 7:
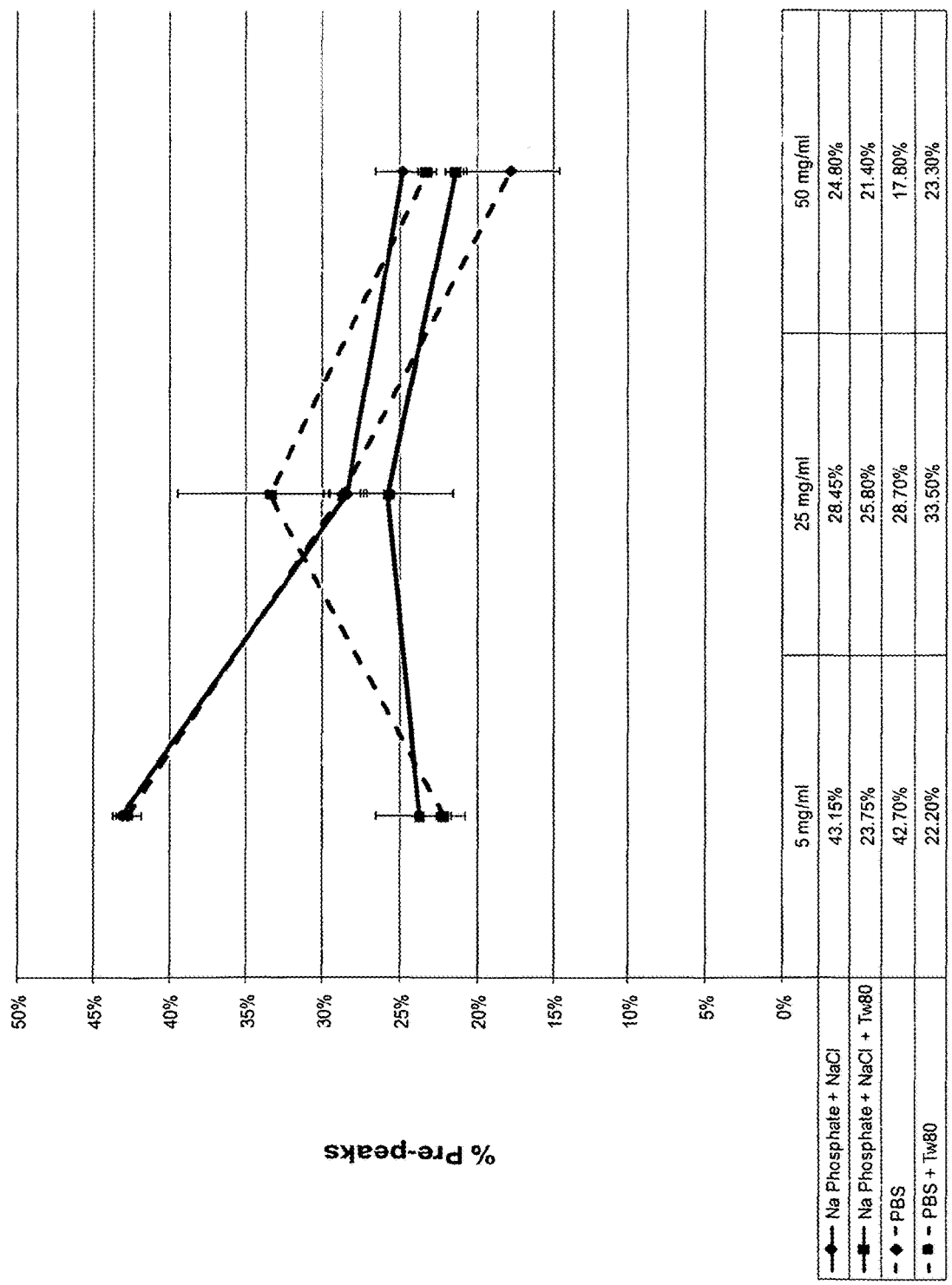

FIG. 7 reports the relative amount of pre-peaks obtained from SE-HPLC analysis of samples before and after nebulization. The total amount of pre-peaks represents the formation of multimeric forms.

The effect of Tween 80 in reducing the percentage of multimeric species is more relevant only at a low concentration of the Nanobody (5 mg/ml).

Example 10: Effect of Selected Buffers on Aerosol Droplet Size of Nanobody RSV434

The buffers selected were $NaH_2PO_4/Na_2HPO_4$ 10 mM pH 7.0+NaCl 0.13 M with or without Tween80 0.04% (w:v); and PBS buffer with or without Tween80 0.04% (w:v). The composition of PBS was 10.14 mM Na2HPO4, 1.76 mM KH2PO4, 2.67 mM KCl and 136.9 mM NaCl with pH 7.8. The concentration of NaCl was adjusted to 0.13M (instead of 0.14M in earlier experiments) in order to ensure an isotonic solution (about 290 mOsm/kg).

Figure 8:
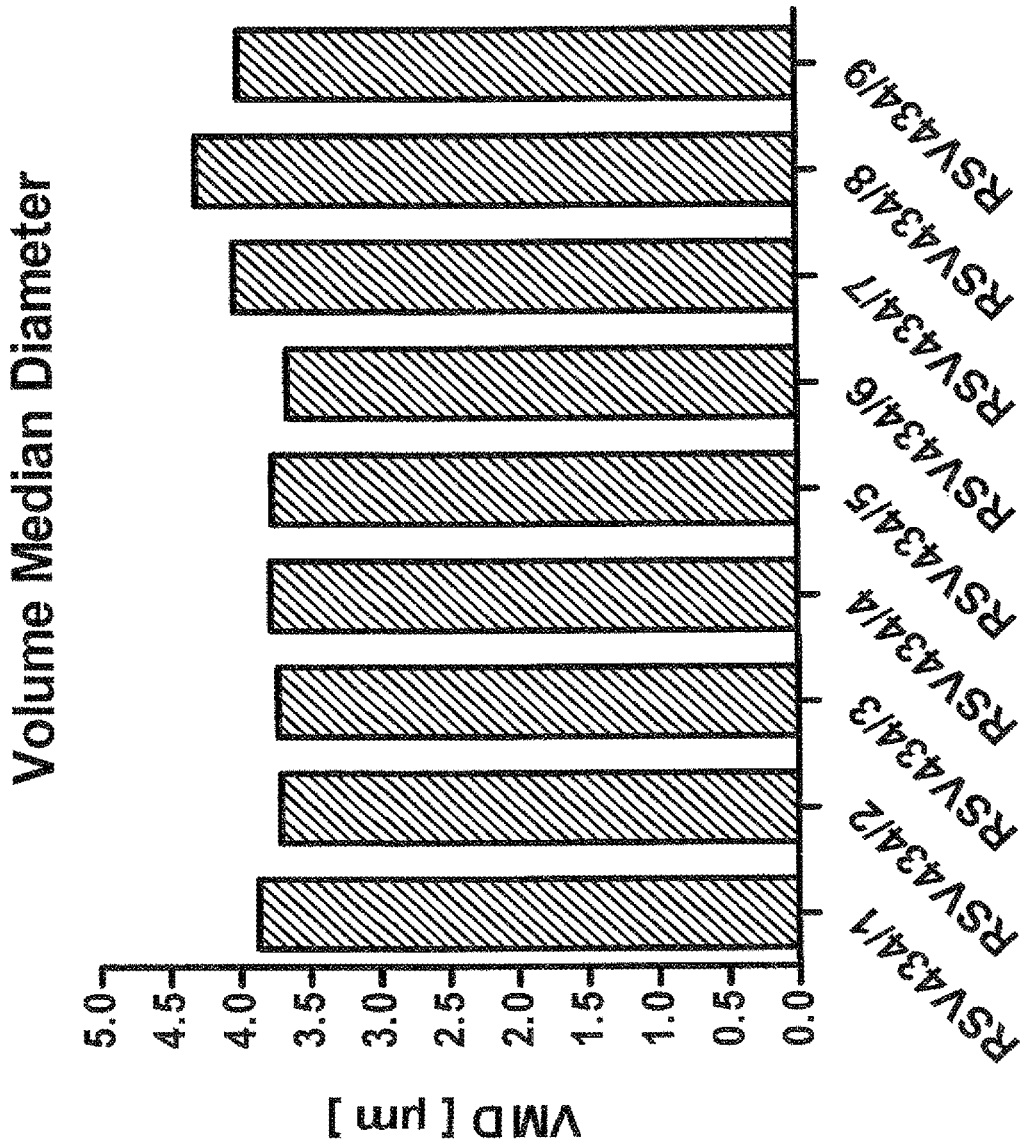

Samples of RSV 434 formulated as described in Table 8 were subjected to nebulization experiments with the Akita[2] APIXNEB® nebulizer device, in order to determine average droplet size (FIG. 8). The nebulizer uses a membrane with a mesh size of 4 µm, so a particle size of 4 µm or less should be achieve after nebulization.

From the data reported in FIG. 8 it appears that the droplet size (Volume Median diameter or VMD, measured by laser diffraction) is reproducible along different formulations and it is suitable for a delivery to the deep lungs (about 4 µm, 3.8 µm for formulations at the concentration of 50 mg/mL).

TABLE 8

Description of samples code, composition and concentration

| Product code | Formulation buffer | Protein concentration |
|---|---|---|
| RSV434/1 | $NaH_2PO_4/Na_2HPO_4$ 10 mM pH 7.0/0.13M NaCl/0.04% Tween 80 | 26.92 mg/mL |
| RSV434/2 | PBS | 51.23 mg/mL |
| RSV434/3 | PBS + 0.04% Tween 80 | 52.15 mg/mL |
| RSV434/4 | $NaH_2PO_4/Na_2HPO_4$ 10 mM pH 7.0 0.13M NaCl | 50.82 mg/mL |
| RSV434/5 | $NaH_2PO_4/Na_2HPO_4$ 10 mM pH 7.0/0.13M NaCl/0.04% Tween 80 | 51.86 mg/mL |
| RSV434/6 | PBS | 4.88 mg/mL |
| RSV434/7 | PBS + 0.04% Tween 80 | 5.06 mg/mL |
| RSV434/8 | $NaH_2PO_4/Na_2HPO_4$ 10 mM pH 7.0 0.13M NaCl | 4.98 mg/mL |
| RSV434/9 | $NaH_2PO_4/Na_2HPO_4$ 10 mM pH 7.0/0.13M NaCl/ 0.04% Tween 80 | 5.06 mg/mL |

Example 11: Effect of Protein Concentration on Molecular Weight of Aggregates Formed in Nebulized Material of Nanobody RSV434

Additional nebulization experiments (in triplicate) were performed on RSV 434 solution at the concentration of 5 and 50 mg/mL, formulated in NaH2PO4/Na2HPO4 10 mM pH 7.0+NaCl 0.13M, with the following concentrations of surfactant: 0, 0.02% w/v and 0.04% w/v.

Each sample was nebulized as in the previous experiments, with the exception of the collection procedure, which was performed using a glass container (100 ml bottle).

SE-HPLC analysis of the samples after nebulization allows quantifying the relative amount of multimeric forms (pre-peaks) of RSV 434 (see Table 9).

No significant influence of Tween 80 on the percentage of multimeric forms after nebulization could be seen when the Nanobody was at a concentration of 50 mg/mL. At the lower concentration (5 mg/mL), the presence of Tween 80 (0.02% and 0.04% w/v) halved the percentage of total pre-peaks in the nebulized material.

Figure 9:
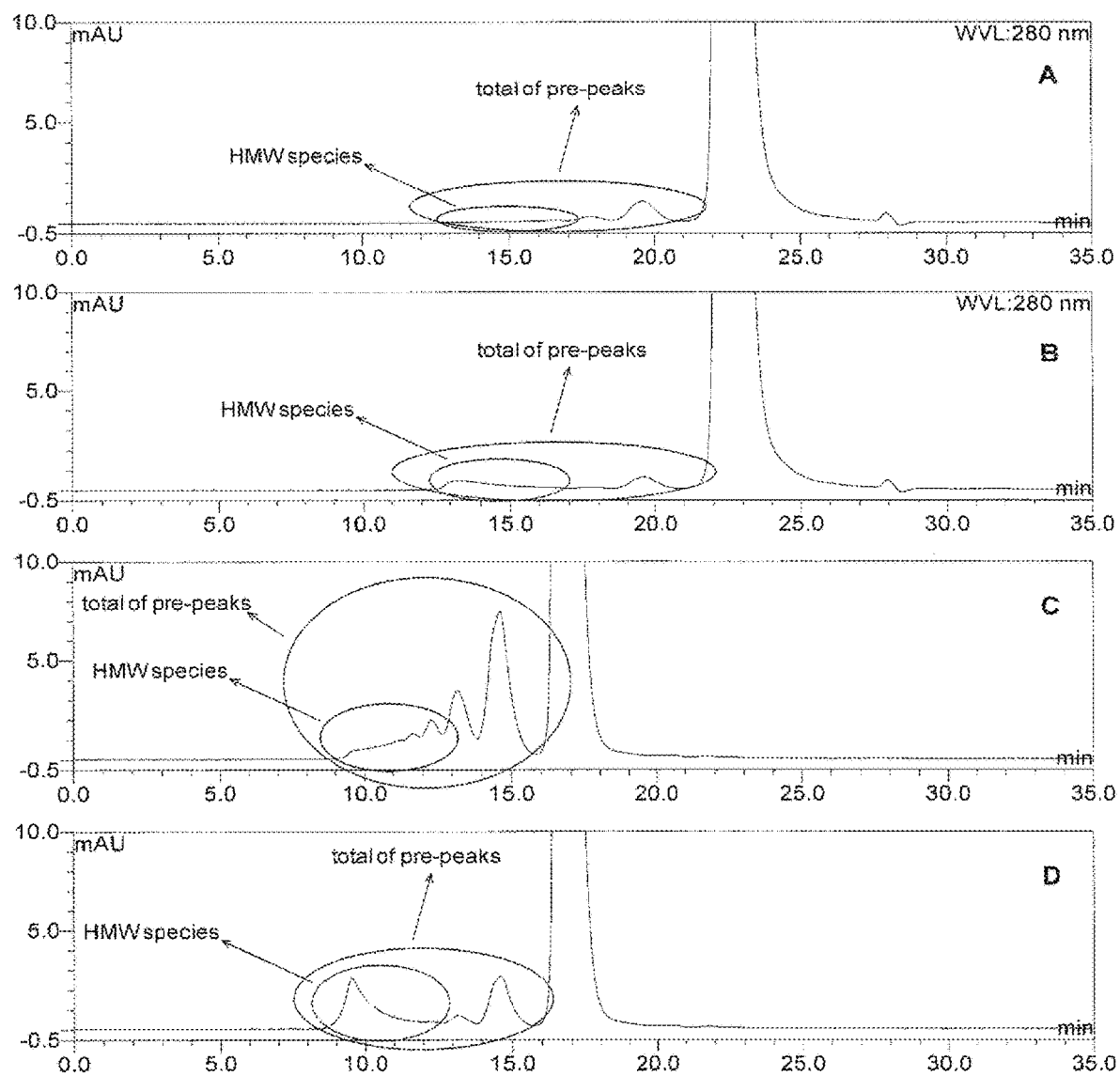

Analyzing in detail the SE-HPLC chromatograms, it was possible to determine also the relative amount of high molecular weight (HMW) species in the pre-peaks region (see Table 9 and FIG. 9); HMW aggregates of RSV434 correspond to aggregates detected in size exclusion chromatography having a molecular weight of more than about 200 kDa. The results clearly show that at 50 mg/mL less HMW species are formed in formulations without Tween 80. At 5 mg/ml no difference was observed.

TABLE 9

Percentage (%) of total pre-peaks and percentage (%) of high molecular weight (HMW) species (calculated from integration data of SE-HPLC chromatograms - see FIG. 9) before and after nebulization of RSV 434 at the concentration of 50 mg/mL and 5 mg/mL (n = 3)

| RSV434 | | | % of total pre-peaks | % of HMW species (pre-peak 1) |
|---|---|---|---|---|
| 50 mg/mL | No Tween 80 | REF | 0.19 | 0.01 |
| | | NEB | 1.03 | 0.15 |
| | 0.02% Tween 80 | REF | 0.19 | 0.03 |
| | | NEB | 1.35 | 0.79 |
| | 0.04% Tween 80 | REF | 0.20 | 0.04 |
| | | NEB | 1.07 | 0.51 |
| 5 mg/mL | No Tween 80 | REF | 1.4 | 0.4 |
| | | NEB | 11.6 | 3.1 |

TABLE 9-continued

Percentage (%) of total pre-peaks and percentage (%) of high molecular weight (HMW) species (calculated from integration data of SE-HPLC chromatograms - see FIG. 9) before and after nebulization of RSV 434 at the concentration of 50 mg/mL and 5 mg/mL (n = 3)

| RSV434 | | % of total pre-peaks | % of HMW species (pre-peak 1)

-continued

Gln Gly Thr Leu Val Thr Val Ser Ser Gly Gly Gly Ser Gly Gly
            245                 250                 255

Gly Ser Glu Val Gln Leu Leu Glu Ser Gly Gly Gly Leu Val Gln Pro
        260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320

Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 2
<211> LENGTH: 408
<212> TYPE: PRT
<213> ORGANISM: Artificial Sequence
<220> FEATURE:
<223> OTHER INFORMATION: Nanobody

<400> SEQUENCE: 2

Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Thr Ala Val Tyr Tyr Cys
            85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Gly Ser Gly Gly Gly Ser Glu Val Gln
        130                 135                 140

Leu Val Glu Ser Gly Gly Gly Leu Val Gln Ala Gly Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
            275                 280                 285

Ser Gly Gly Gly Leu Val Gln Ala Gly Gly Ser Leu Ser Ile Ser Cys
290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
            325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
355                 360                 365

Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
            405

<210> SEQ ID NO 3
<211> LENGTH: 408
<212> TYPE: PRT
<213> ORGANISM: Artificial Sequence
<220> FEATURE:
<223> OTHER INFORMATION: Nanobody

<400> SEQUENCE: 3

Glu Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
            35                  40                  45

Ala Ala Ile Asn Trp Arg Gly Asp Ile Thr Ile Gly Pro Pro Asn Val
50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
            115                 120                 125

Gly Gly Ser Gly Gly Gly Gly Ser Gly Gly Gly Ser Glu Val Gln
            130                 135                 140

Leu Val Glu Ser Gly Gly Gly Leu Val Gln Ala Gly Gly Ser Leu Ser
145                 150                 155                 160

```
Ile Ser Cys Ala Ala Ser Gly Gly Ser Leu Ser Asn Tyr Val Leu Gly
            165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
            195                 200                 205

Phe Thr Ile Ser Arg Asp Asn Ala Lys Asn Thr Gly Tyr Leu Gln Met
        210                 215                 220

Asn Ser Leu Ala Pro Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Gly Ser Leu Ser Ile Ser Cys
        290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
            355                 360                 365

Ala Pro Asp Asp Thr Ala Val Tyr Tyr Cys Gly Ala Gly Thr Pro Leu
        370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405
```

The invention claimed is:

1. A method for reducing the percentage of aggregate formation in atomized material of immunoglobulin single variable domains comprising atomizing in a vibrating-mesh nebulizer a first composition comprising an aqueous carrier and a polypeptide comprising one or more immunoglobulin single variable domains, wherein:
   the concentration of the polypeptide comprising one or more immunoglobulin single variable domains present in the first composition is 50 mg/mL or more, wherein the aqueous carrier comprises saline (NaCl 0.9%), histidine, or phosphate buffered saline; and
   the percentage of aggregate formation in the atomized material, as determined by SE-HPLC, is reduced compared to: (a) the percentage of aggregate formation in atomized material obtained from atomizing in a vibrating-mesh nebulizer a second composition comprising an aqueous carrier and the polypeptide comprising one or more immunoglobulin single variable domains at a concentration of 5 mg/mL; or (b) the percentage of aggregate formation in atomized material obtained from atomizing in a jet nebulizer a third composition comprising an aqueous carrier and the polypeptide comprising one or more immunoglobulin single variable domains.

2. The method of claim 1, wherein the first composition further comprises a surfactant at a concentration between 0.001% and 1%.

3. The method of claim 2, wherein the surfactant is selected from polysorbates and poloxamers, or wherein PEG is added as a surfactant-like compound.

4. The method of claim 1, wherein the polypeptide comprising one or more immunoglobulin single variable domains is present in the first composition at a concentration of 50 mg/mL to 200 mg/mL and wherein the first composition does not comprise a surfactant.

* * * * *

UNITED STATES PATENT AND TRADEMARK OFFICE
CERTIFICATE OF CORRECTION

| | | |
|---|---|---|
| PATENT NO. | : 11,007,146 B2 | Page 1 of 1 |
| APPLICATION NO. | : 15/495199 | |
| DATED | : May 18, 2021 | |
| INVENTOR(S) | : Depla et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 574 days.

Signed and Sealed this
Twenty-fourth Day of January, 2023

Katherine Kelly Vidal
*Director of the United States Patent and Trademark Office*